(12) United States Patent
Barker et al.

(10) Patent No.: US 10,195,304 B2
(45) Date of Patent: Feb. 5, 2019

(54) FUNCTIONALIZED MICROGELS WITH FIBRIN BINDING ELEMENTS

(71) Applicant: Georgia Tech Research Corporation, Atlanta, GA (US)

(72) Inventors: Thomas H. Barker, Atlanta, GA (US); Ashley Carson Brown, Atlanta, GA (US); Louis Andrew Lyon, Irvine, CA (US); Sarah E. Stabenfeldt, Tempe, AZ (US); Nicole Welsch, Berlin (DE)

(73) Assignee: Georgia Tech Research Corporation, Atlanta, GA (US)

( * ) Notice: Subject to any disclaimer, the term of this patent is extended or adjusted under 35 U.S.C. 154(b) by 201 days.

(21) Appl. No.: 15/035,831

(22) PCT Filed: Nov. 11, 2014

(86) PCT No.: PCT/US2014/065053
§ 371 (c)(1),
(2) Date: May 11, 2016

(87) PCT Pub. No.: WO2015/070233
PCT Pub. Date: May 14, 2015

(65) Prior Publication Data
US 2016/0271292 A1   Sep. 22, 2016

Related U.S. Application Data

(60) Provisional application No. 61/902,489, filed on Nov. 11, 2013.

(51) Int. Cl.
| C07K 16/00 | (2006.01) |
| A61L 24/00 | (2006.01) |
| A61L 27/22 | (2006.01) |
| A61L 26/00 | (2006.01) |
| A61L 24/04 | (2006.01) |
| A61L 24/06 | (2006.01) |

(52) U.S. Cl.
CPC ......... *A61L 24/0015* (2013.01); *A61L 24/046* (2013.01); *A61L 24/06* (2013.01); *A61L 26/0047* (2013.01); *A61L 27/227* (2013.01); *A61L 2300/418* (2013.01); *A61L 2400/04* (2013.01)

(58) Field of Classification Search
None
See application file for complete search history.

(56) References Cited

FOREIGN PATENT DOCUMENTS

| GB | 2431104 | 4/2007 |
| WO | 2009079664 | 6/2009 |
| WO | 2012150254 | 11/2012 |

OTHER PUBLICATIONS

Mariuzza et al (Annu. Rev. Biophys. Biophys. Chem. 1987; 16: 139-159).*
Muyldermans (ARB, 82:17.1-17.23, 2013).*
Bertram, et al., "Intravenous hemostat: nanotechnology to halt bleeding", Sci Transl Med., 1 (11):11ra22, 16 pages (2009).
Clemetson, "Platelets and primary haemostasis", Thromb Res., 129:220-4 (2012).
Ersoy, et al., "Hemostatic effects of microporous polysaccharide hemosphere in a rat model with severe femoral artery bleeding", Adv Ther, 24:485-492 (2007).
Fries, et al., "Role of fibrinogen in trauma-induced coagulopathy", Br J Anaesth, 105:116-21 (2010).
Fuglsang, et al., "Platelet activity and in vivo arterial thrombus formation in rats with mild hyperhomocysteinaemia", Blood Coagul Fibrinolysis, 13:683-9 (2002).
Gao, et al., "Influence of reaction conditions on the synthesis of self-cross-linked N-isopropylacrylamide microgel\s", Langmuir, 19:5217-22 (2003).
Geeraedts, et al., "Exsanguination in trauma: A review of diagnostics and treatment options", Injury, 40:11-20 (2009).
Granville-Chapman, et al., "Pre-hospital haemostatic dressings: a systematic review", Injury, 42:447-59 (2011).
Jackson, et al., "Dynamics of platelet thrombus formation", J Thromb Haemost : Suppl 1:17-20 (2009).
Modery-Pawlowski, et al., "Approaches to synthetic platelet analogs", Biomaterials, 34:526-541 (2013).
Sauaia, et al., "Epidemiology of trauma deaths: a reassessment", J Trauma, 38:185-93 (1995).
Suzuki-Inoue, et al., "Involvement of Src kinases and PLCgamma2 in clot retraction", Thromb Res, 120:251-258 (2007).
Thomas, et al., "Studies on the actin-binding protein HS1 in platelets", BMC Cell Biology, 8:46 (2007).
International Search Report for corresponding PCT application PCT/US2014/065053 dated Mar. 27, 2015.

* cited by examiner

*Primary Examiner* — Brad Duffy
(74) *Attorney, Agent, or Firm* — Smith, Gambrell & Russell, LLP; Charles Vorndran

(57) ABSTRACT

Ultra-low crosslinked microgels made of an ultra-low crosslinked polymer are provided. The microgels, also referred to as Platelet-like Particles (PLPs), preferably have <0.5% crosslinking densities. One or more of the polymers are conjugated with a fibrin-binding element or moiety, preferably H6, in an amount effective to confer to the microgel selective binding to fibrin under physiological conditions. The PLPs can recapitulate multiple key functions of platelets including binding, stabilizing and enhancing fibrin clot formation, responsiveness to injury cues, and induction of clot contraction. In a preferred embodiment, the microgel or PLP has little or no binding to soluble fibrinogen under physiological conditions compared to its binding to fibrin. The microgels or PLPs are prepared using crosslinker-free synthesis conditions, and can promote or induce clotting and clot contraction.

11 Claims, 11 Drawing Sheets

Specification includes a Sequence Listing.

SEQUENCE LISTING

```
<160> NUMBER OF SEQ ID NOS: 5

<210> SEQ ID NO 1
<211> LENGTH: 144
<212> TYPE: PRT
<213> ORGANISM: Artificial Sequence
<220> FEATURE:
<223> OTHER INFORMATION: Polypeptide

<400> SEQUENCE: 1

Gln Val Gln Leu Leu Glu Ser Gly Gly Gly Leu Val Gln Pro Gly Gly
1               5                   10                  15

Ser Leu Arg Leu Ser Cys Ala Ala Ser Gly Asp Arg Phe Thr His Asn
            20                  25                  30

Asp Met Gly Trp Val Arg Gln Ala Pro Gly Lys Gly Leu Glu Trp Val
        35                  40                  45

Ser Thr Ile Pro Thr Thr Asp Gly Ser Thr Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Tyr Met Trp Lys Ala Pro Ala Tyr Val Lys Tyr Trp Gly
            100                 105                 110

Gln Gly Thr Leu Val Thr Val Ser Ser Ala Ala Ala Glu Gln Lys Leu
        115                 120                 125

Ile Ser Glu Glu Asp Leu Asn Ser Ala Ala His Tyr Thr Asp Ile Gly
    130                 135                 140

<210> SEQ ID NO 2
<211> LENGTH: 142
<212> TYPE: PRT
```

<213> ORGANISM: Artificial Sequence
<220> FEATURE:
<223> OTHER INFORMATION: Polypeptide

<400> SEQUENCE: 2

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Asn Asp Lys
            20                  25                  30

Ile Met Thr Trp Val Arg Gln Ala Pro Gly Lys Gly Leu Glu Trp Val
        35                  40                  45

Ser Ser Ile Ser Gly Pro Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Cys Ala Ala Ser Ser Thr Met Glu Tyr Trp Gly Gln Gly
            100                 105                 110

Thr Leu Val Thr Val Ser Ser Ala Ala Ala Glu Gln Lys Leu Ile Ser
            115                 120                 125

Glu Glu Asp Leu Asn Ser Ala Ala His Tyr Thr Asp Ile Arg
            130                 135                 140

<210> SEQ ID NO 3
<211> LENGTH: 146
<212> TYPE: PRT
<213> ORGANISM: Artificial Sequence
<220> FEATURE:
<223> OTHER INFORMATION: Polypeptide

<400> SEQUENCE: 3

Gln Val Gln Leu Leu Glu Ser Gly Gly Gly Leu Val Gln Pro Gly Gly
1               5                   10                  15

Ser Leu Arg Leu Ser Cys Ala Ala Ser Gly Val Arg Ile Thr Asp Asp
            20                  25                  30

Ser Met Ser Trp Val Arg Gln Ala Pro Gly Lys Gly Leu Glu Trp Val
        35                  40                  45

Ser Ser Ile Glu Asp Asn Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Glu Gly Trp Asp Val Leu Arg Arg Asp Gln Ala Val Thr Ser
            100                 105                 110

Trp Gly Gln Gly Thr Leu Val Thr Val Ser Ser Ala Ala Ala Glu Gln
            115                 120                 125

Lys Leu Ile Ser Glu Glu Asp Leu Asn Ser Ala Ala His Tyr Thr Asp
            130                 135                 140

Met Arg
145

<210> SEQ ID NO 4
<211> LENGTH: 5
<212> TYPE: PRT
<213> ORGANISM: Artificial Sequence
<220> FEATURE:

```
<223> OTHER INFORMATION: Tumor-homing pentapeptide

<400> SEQUENCE: 4

Cys Arg Glu Lys Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Fibrin targeting peptide

<400> SEQUENCE: 5

Gly Pro Arg Pro Phe Pro Ala Cys
1               5
```

FUNCTIONALIZED MICROGELS WITH FIBRIN BINDING ELEMENTS

CROSS-REFERENCE TO RELATED APPLICATIONS

This application is a 371 application of International Application No. PCT/US2014/065053, filed Nov. 11, 2014, which claims priority to and benefit of U.S. Provisional Patent Application No. 61/902,489 filed on Nov. 11, 2013, and where permissible, is incorporated herein in its entirety.

STATEMENT REGARDING FEDERALLY SPONSORED RESEARCH

This invention was made with Government support under Contract Number EB013743 awarded by the National Institutes of Health, Contract No. W81XWGH110306 awarded by the U.S. Army. The Government has certain rights in the invention.

REFERENCE TO SEQUENCE LISTING

The Sequence Listing submitted as a text file named "GTRC_6227_ST25_2_Corrected.txt," created on Feb. 9, 2015, and having a size of 4,735 bytes is hereby incorporated by reference pursuant to 37 C.F.R. § 1.52(e)(5).

FIELD OF THE INVENTION

The invention is generally directed to microgels, more specifically to microgels containing fibrin binding moieties.

BACKGROUND OF THE INVENTION

Uncontrolled bleeding is the major cause of death in civilian and battlefield traumas, Sauaia, et al., *The Journal of Trauma*, 38:185-193 (1995); Geeraedts, et al., *Injury*, 40:11-20 (2009), highlighting the critical need for better technologies for wound management. Current hemostasis technologies, including topical sealants, exothermic zeolites, advanced dressings and recombinant clotting factors, Clemetson, K. J., *Thrombosis Research*, 129:220-224 (2012); Fries, et al., *British Journal of Anaesthesia*, 105:116-121 (2010), have demonstrated modest successes, yet all have significant drawbacks and none are as 'evolved' as the natural hemostasis system. More recent efforts have focused on the creation of synthetic analogues of clotting constituents, most notably platelets. The vital platelet functions, McGwin, et al., *The Journal of Trauma*, 66:526-530 (2009); Granville-Chapman, et al., *Injury*, 42:447-459 (2011), that one would like to recapitulate include binding, stabilization and enhancement of fibrin clot formation in dynamic flow conditions; clot contraction; and cytokine and growth-factor release to stimulate wound healing. So far, all artificial platelet approaches, ranging from purely synthetic to reconstituted freeze dried harvested native platelets, fail to fully recapitulate these key functions. Most approaches claiming success achieve only the binding and augmentation of clot formation through multivalent display of platelet-binding motifs or platelet-cell surface adhesion motifs on a micro/nano-sized vehicle, Evans, et al., *World Journal of Surgery*, 34:158-163 (2010).

Such approaches are sufficient to recruit clotting components and thereby decrease clotting time; however, these studies rely on vehicles that lack the natural platelet's ability to deform within and in response to the fibrin mesh.

Therefore, it is an object of the invention to provide compositions and methods display platelet-like behaviors.

It is another object of the invention to provide compositions and methods for increasing hemostatsis.

It is another object of the invention to provide compositions and methods for promoting clot contraction.

SUMMARY OF THE INVENTION

Ultra-low crosslinked microgels made of an ultra-low crosslinked polymer are provided. The microgels, also referred to as Platelet-like Particles (PLPs), preferably have <0.5% crosslinking densities. One or more of the polymers are conjugated with a fibrin-binding element or moiety, preferably H6, in an amount effective to confer to the microgel selective binding to fibrin under physiological conditions. The PLPs can recapitulate multiple key functions of platelets including binding, stabilizing and enhancing fibrin clot formation, responsiveness to injury cues, and induction of clot contraction. In a preferred embodiment, the microgel or PLP has little or no binding to soluble fibrinogen under physiological conditions compared to its binding to fibrin. The microgels or PLPs are prepared using crosslinker-free synthesis conditions, and can promote or induce clotting and clot contraction.

Pharmaceutical compositions including the fibrin-binding microgels are also provided. The pharmaceutical compositions can be used to promote or induce hemostasis. One embodiment provides a method for promoting or inducing hemostasis in a subject in need thereof by administering an effective amount of the microgel composition to promote or induce clotting in the subject. The composition also induces or promotes clot contraction in the subject.

Another embodiment provides a medical device coated with the fibrin-binding microgels. The medical device can be a clamp, suture, or wound dressing or any other medical device used to control bleeding. The wound dressing can be any conventional wound dressing having the microgels applied to the wound dressing, impregnated in the wound dressing, or attached to the wound dressing in an amount effective to promote or induce hemostasis when the wound dressing in applied to a wound.

Another embodiment provides a method for making platelet-like particles including the steps of polymerizing a polymer under crosslinker free conditions to form platelet-like particles, and conjugating to the platelet-like particles to a binding moiety specific for fibrin, wherein the binding moiety specific for fibrin has little or no binding to soluble fibrinogen under physiological conditions.

Still another embodiment provides a method for inducing clotting in a tumor, by administering to the tumor an effective amount of the microgels to increase clotting in the tumor. Solid tumors are known to undergo rapid angiogenesis to produce dysfunctional leaky vessels which results in activation of the clotting cascade. To limit nutrient delivery to the tumor, clotting can be induced by PLPs to inhibit blood supply to the tumor. In addition to this, PLPs can be used to deliver anti-tumor agents.

Another embodiment provides a method for treating a wound by administering to the wound an effective amount of the microgels to promote or enhance hemostasis. The wound can be a normal wound, chronic wound or fibrotic wound.

BRIEF DESCRIPTION OF THE DRAWINGS

FIGS. 2B-2K are representative SPR sensorgrams of scFvs on fibrin layer (FIGS. 2B-2F) or BSA surface (FIGS. 2G-2K) for clones A2 (FIGS. 2B and 2G), A6 (FIGS. 2C and 2H), H6 (FIGS. 2D and 2K), B3 (FIGS. 2E and 2J), or non-specific control (FIGS. 2F and 2K). Experimental data is shown in black and fits are shown in dotted line.

FIG. 4A shows increased magnification images of PLPs, natural platelets (PRP), S11-ULCs, and H6-polystyrene (H6-PS) within fibrin matrices 1 h post-polymerization. FIG. 4B shows confocal images of clots analysed 1 h (Day 1) or 24 h (Day 2) post-polymerization. Owing to increased fibrin density in PRP and PLP clots, exposure times equivalent to those of fibrin-only and S11-ULC clots resulted in signal saturation. To allow appreciation of the network structure in the presence of saturation, 0.33× exposures and equivalent exposures are shown on the left- and right-hand sides, respectively, of the images for PRP and PLP clots.

DETAILED DESCRIPTION OF THE INVENTION

I. Definitions

As used herein, "polymer" refers to a molecule consisting of a number of repeating units.

As used herein, "repeat unit" refers to the fundamental recurring unit of a polymer.

As used herein, "monomer" refers to the smaller molecule(s) that are used to prepare a polymer. It may or may not be equivalent to the repeat unit.

As used herein, "macromer" and "macromonomer" refers to any polymer or oligomer that has a functional group that can take part in further polymerization.

As used herein, "microgel" refers to a gel formed from a network of microscopic filaments of polymer or macromer.

As used herein, "subject or patient" refers to a mammal, primate and preferably a human.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

II. Platelet-Like Particles

Figure 1:
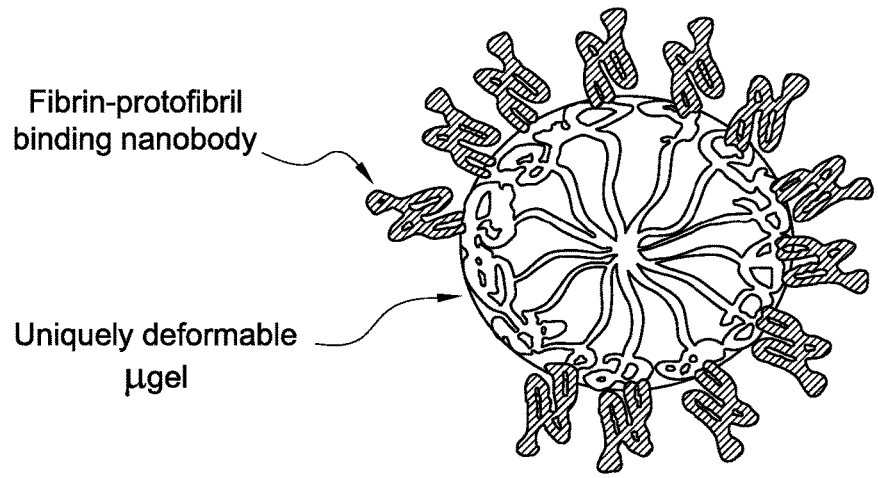
FIG. 1 is a schematic of a representative of one embodiment of a fibrin-binding microgel or platelet-like particle.
Figure 2A:
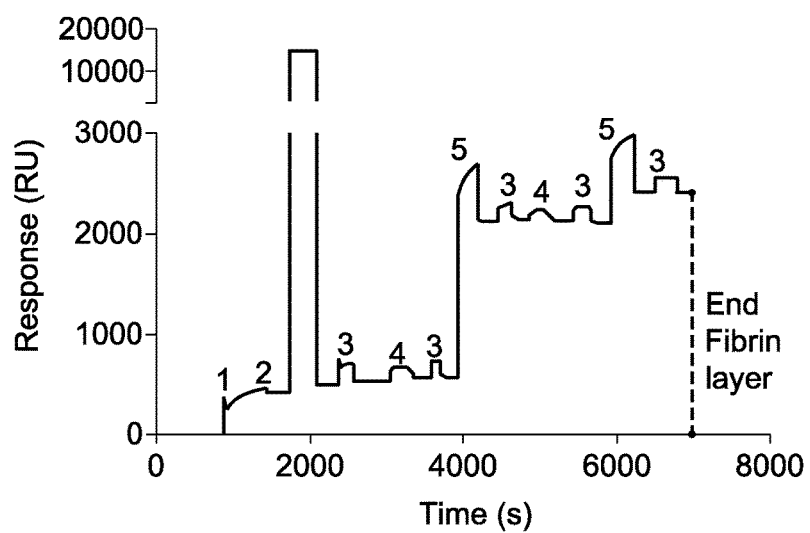
FIG. 2A is an SPR sensorgram of thin fibrin layer immobilized on surface the SPR channel via NHS/EDC activated carboxylic acid terminated SAM with subsequent injections of fibrinogen (1), ethanolamine quencher (2), HEPES buffer+Tween 20 (3), thrombin (4), and fibrinogen+anti-thrombin+heparin (5).
Figure 2B:
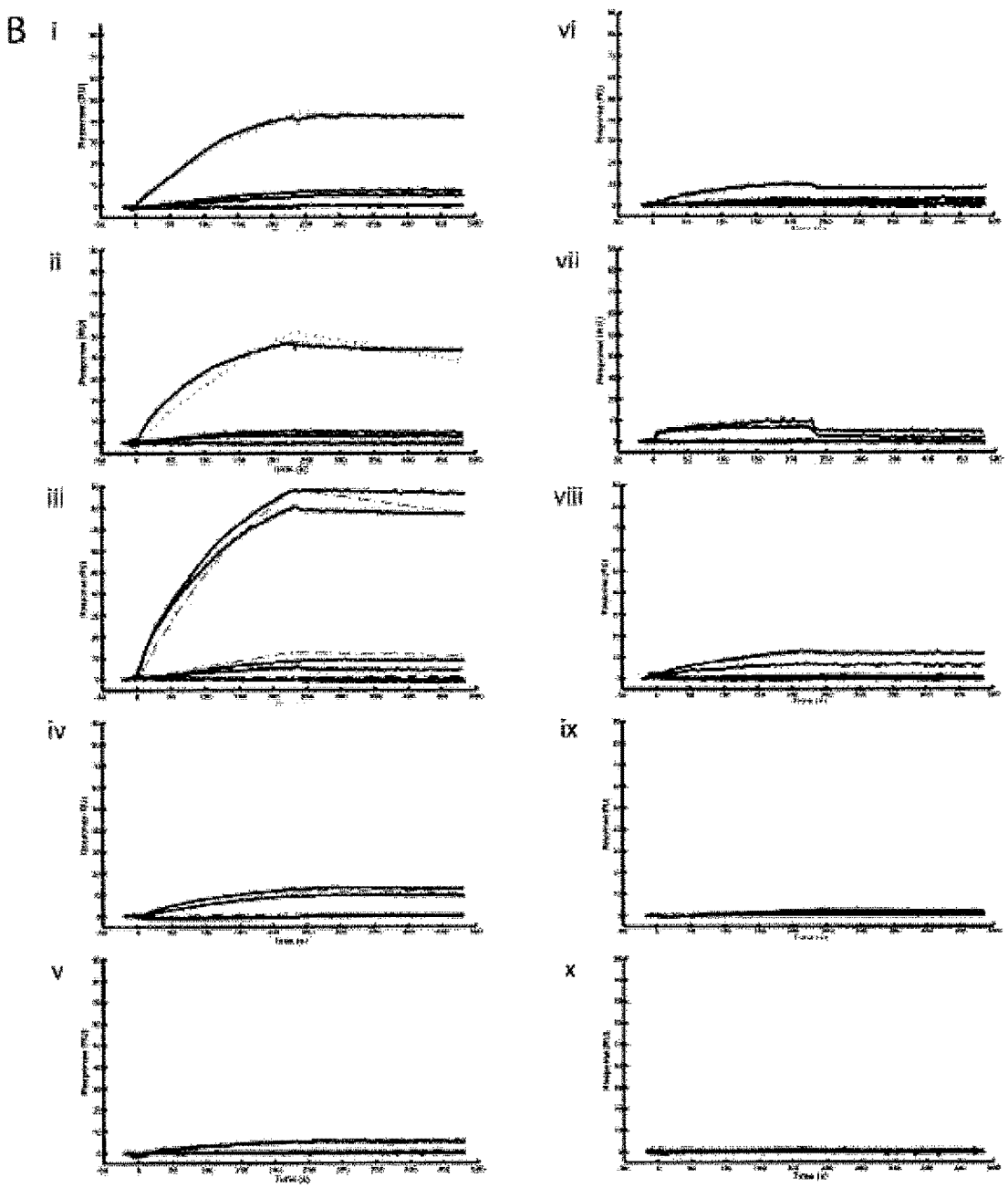

Ultra-low crosslinked (ULC) microgels that bind to fibrin under physiological conditions are provided. In one embodiment, the microgels were synthesized via a non-standard, 'crosslinker free', precipitation polymerization method, Modery-Pawlowski, et al., *Biomaterials*, 34:526-541 (2013). This unique method leverages rare chain-transfer associated chain branching events to create microgels with exceedingly low (<0.5%) crosslinking densities resulting in particles with an unmatched deformability, Gao, et al., *Langmuir*, 19:5217-5222 (2003). The microgels have a fibrin binding moiety conjugated to the polymer used to form the microgel (FIG. 1). These microgels that specifically bind to fibrin are also referred to as Platelet-like Particles (PLPs). In a preferred embodiment, the PLPs target fibrin, but not the soluble precursor fibrinogen, with high affinity and specificity. The PLPs are therefore more specific to sites of injury than any previously described platelet-mimicking materials.

Additionally, the PLPs can recapitulate multiple key functions of platelets including binding, stabilizing and enhancing fibrin clot formation, responsiveness to injury cues, and induction of clot contraction.

In another embodiment, the platelet-like particles contain or have cytokines and/or growth factors releaseably attached to the particles so that the cytokines and/or growth factors can be released at wound sites to stimulate wound healing.

It was unexpectedly discovered that the PLPs could induce clot contraction. High affinity for fibrin coupled with high particle deformability are important for the PLPs to obtain clot contraction. Platelets naturally bind strongly to their surrounding fibrin matrix through αIIbβ3 integrin-mediated interactions, which facilitates engagement of the actin/myosin machinery, leading to platelet deformation and clot contraction. Although the disclosed PLPs do not have active contractile machinery, they are capable of interacting strongly with the surrounding fibrin matrix, which induces network collapse. The multivalent interactions between microgel polymer chains and fibrin fibers likely cause local deformation of the fibrin network, acting as crosslinkers or bridging sites between adjacent fibers. Such bridging sites likely make subsequent microgel binding more favorable via a cooperative "zipper effect". Over time these multiple small collapses and concomitant microgel binding will lead to an overall (macroscopically observable) network collapse. Recent studies characterizing collapse of actin polymers by myosin demonstrate that actin network connectivity (determined by the degree of crosslinking) controls length scales of contraction, with weakly connected networks contracting locally, medially crosslinked networks contracting into multiple disjointed clusters and strongly crosslinked networks contracting into a single dense cluster, Alvarado, et al., *Nature Physics*, 9:591-597 (2013).

Over time, the disclosed PLPs induce local network contraction, followed by contraction into multiple dense fibrin clusters, ultimately inducing contraction into a single dense fibrin cluster. A few features of the PLPs appear to be important for this process. In one embodiment, the high fibrin affinity imparted by H6 permits the particles to remain bound to the fibers as the clot collapses. The extremely low density of the ULC micogels likely permits the pendant sdFvs to engage fibrin with near-native affinity. In contrast, more densely crosslinked (and therefore not as deformable) particles would restrict the ability of pendant sdFvs to bind to multiple fibers, therefore decreasing the degree of fiber deformation and diminishing the cooperativity of subsequent microgel binding events.

Like natural platelets, the disclosed ULC microgels are approximately 1 μm in diameter in solution. The disclosed ULC microgels can range in size from ~200 nm in diameter to ~40 μm in diameter. Initiation of clotting, platelets become activated, bind to nascent fibrin fibers, actively spread within the fibrin network, and over time engage their actin-myosin machinery to contract the clot. Through the course of these events, platelets undergo significant shape changes. The disclosed ULC microgel platelet 'bodies' are capable of undergoing large degrees of deformation, as suggested by atomic force microscopy (AFM) images of microgel spread on a glass surface with a diameter of approximately 2 μm but an approximate height of only 4 nm.

A. Microgels or PLPs

As discussed above, the microgels contain one or more polymers that are polymerized using a non-standard, 'crosslinker free', precipitation polymerization method, Modery-Pawlowski, et al., *Biomaterials*, 34:526-541 (2013). This method creates microgels with exceedingly low (<0.5%) crosslinking densities, resulting in particles with an unmatched deformability, Gao, et al., *Langmuir*, 19:5217-5222 (2003). ULC microgels also have a fibrin biding moiety conjugated to one or more polymers of the microgel.

1. Polymers

Preferred polymers for producing the microgels include, but are not limited to poly(N-isopropylacrylamideco-acrylic acid) (pNIPAm-AAc), poly ethylene glycol (PEG), PEG acrylates, PEG methacrylates and combinations thereof. Derivatives of PEG can also be used. Examples of PEG derivatives include, but are not limited to, methoxypolyethylene glycol succinimidyl propionate, methoxypolyethylene glycol N-hydroxysuccinimide, methoxypolyethylene glycol aldehyde, methoxypolyethylene glycol maleimide, PEG derivatives with "click" chemistries functional groups and multiple-branched polyethylene glycol.

The precise number of PEG or derivative units depends on the desire porosity of the microgel. In some embodiments, the molecular weight of the PEG or derivative thereof is between about 100 and 500 Da, 100 Da to 1 kDa, 1 and 200 kDa, or between about 1 and 100 kDa, or between about 1 and 50 kDa. For example, the PEG or derivative thereof can have a molecular weight of "N" kDa, wherein N is any integer between 1 and 200.

The PEG or derivative thereof can have a molecular weight of "N" Da, wherein N is any integer between 100 and 200,000. In a particular embodiment, the molecular weight of the PEG or derivative thereof is "N" Da, wherein "N" is between 100 and 50,000.

In specific exemplary embodiments, the PEG or derivative thereof is 10 kDa, 20 kDa, 30 kDa, 40 kDa, or 50 kDa.

Microgels can be made using other polymers provided the polymers can be made with 'crosslinker free', precipitation polymerization methods. Other polymers that can be used include, but are not limited to non-peptidic polymers including polyalkylene glycol polymers, polyalkylene oxide homopolymers such as polypropylene glycols, polyoxyethylenated polyols, copolymers thereof and block copolymers thereof, as well as poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine) and copolymers, terpolymers, poly-(N-vinylformamide) and mixtures thereof.

2. Methods of Making Microgels

Ultralow crosslinked microgels were made according to the procedure of Gao, J. F., B. J. Influence of reaction conditions on the synthesis of self-crosslinked N-isopropylacrylamide microgels. *Langmuir* 19, 5217-5222 (2003) which is incorporated herein by reference in its entirety. As described in the Examples, in one embodiment a 95% pNIPAm/5% AAc composition (poly(N-isopropylacrylamide-co-acrylic acid) was utilized for microgel synthesis which results in microscaffolds ~1-am diameter in the swollen state. Co-polymerization with acrylic acid was utilized to allow for carboxylic acid chemoligation sites for sdFv attachment, Fries, et al., *British Journal of Anaesthesia*, 105:116-121 (2010); Granville-Chapman, et al., *Injury*, 42:447-459 (2011). Following synthesis, microgels were purified using ultracentrifugation and conjugated to fibrin specific sdFvs using standard EDC/NHS chemistry. For confocal fluorescence microscopy experiments, sdFvs were also labeled with maleimide-Alexa Fluor-488 following conjugation to the microgels.

B. Fibrin Binding Moieties

Fibrin-binding moieties are known in the art. Additionally, as discussed in the Examples, fibrin-binding peptides, antibodies, or fibrin-binding antibody fragments were identified using biopanning as described below.

1. Representative Binding Moieties

Representative fibrin-binding moieties are provided in Table 1 in the Examples. In a preferred embodiment, the fibrin biding moieties are polypeptides encoded by clones A2, A6, B3 and H6. H6 is the most preferred fibrin-binding moiety because it demonstrates a high affinity for fibrin and negligible binding to soluble fibrinogen.

The amino acid sequence for H6 is

```
                                            (SEQ ID NO: 1)
QVQLLESGGGLVQPGGSLRLSCAASGDRFTHNDMGWVRQAPGKGLEW

VSTIPTTDGSTYYADSVKGRFTISRDNSKSTLYLQMNSLRAEDTAVYYCA

TGYMWKAPAYVKYWGQGTLVTVSSAAAEQKLISEEDLNSAAHYTDIG.
```

The amino acid sequence for A2 is

```
                                            (SEQ ID NO: 2)
QVQLLESGGGLVQPGGSLRLSCAASGFSLNDKIMTWVRQAPGKGLEWV

SSISGPNGSTYYADSVKGRFTISRDNSKNTLYLQMNSLRAEDTAVYYCAG

CAAASSTMEYWGQGTLVTVSSAAA EQKLISEEDLNSAAHYTDIR.
```

The amino acid sequence for A6 is

```
                                            (SEQ ID NO: 3)
QVQLLESGGGLVQPGGSLRLSCAASGVRITDDSMSWVRQAPGKGLEWV

SSIEDNSGSTYYADSVKGRFTISRDNSKNTLYLQMNSLRAEDTAVYYCAG

EGWDVLRRDQAVTSWGQGTLVTVSSAAAEQKLISEEDLNSAAHYTDMR.
```

In one embodiment, the microgel has a binding moiety specific for fibrin is present on the surface of the microgel at a density of about $9.98 \times 10^{-11}$ mg/particle. In other embodiments, the density of the binding moiety is optimized to maximized binding specificity of the microgel to fibrin.

2. Methods of Making Binding Moieties

As described in the Examples, fibrin-binding moieties were isolated using phage biopanning against fibrin. The biopanning identified humanized single domain variable fragment antibodies (sdFvs) and single chain variant fragments (scFvs). Three different phagemid libraries were screened in vitro against fibrin clots. Phage particles were produced, then purified prior to beginning the screen. Fibrin clots derived from human plasma were prepared for phage incubation. After incubation, the supernatant containing unbound phage was removed and the fibrin clot was rinsed. Elution of the fibrin binding phage followed an incubation with soluble fibrinogen to remove fibrinogen preferring phage. Bacterial cells were then infected with eluted phage to generate an enriched fibrin-binding population for the next biopanning screen. Following three rounds of screening, 96 clones were evaluated via ELISAs to identify sdFvs that selectively bound to fibrin but not fibrinogen coated plates. Fibrin binding kinetics were then evaluated via SPR.

III. Methods of Using the Platelet-Like Particles

A. Hemostasis

The disclosed microgels or PLPs can be used to induce, promote or increase hemostasis in a subject, preferably a human. By increasing hemostasis in the subject, bleeding or bloods loss is reduced. One embodiment provides a method of promoting or increasing in subject in need thereof by administering to a subject in need thereof, an effective amount of the disclosed microgels that specifically bind to fibrin and have low or no binding to soluble fibrinogen to reduce blood loss or bleeding or to promote or increase clot formation in the subject. The microgels can be administered intravenously, parenterally or topically depending on whether the bleeding is internal or through the skin. Studies have demonstrated a does of 100 mg/kg of PLPs delivered intravenously is effective to augment hemostasis in rodents following traumatic injury.

Another embodiment provides a method of promoting or increasing clot contraction in a subject in need thereof, by administering an effective amount of the microgels or PLPs to increase clot contraction in the subject relative to a control microgel or PLP. Control microgels can be microgels that do not contain a fibrin-binding moiety.

The microgels can be administered to any type of wounds to promote hemostasis. The wound can be internal or external. For example, the wound can be caused by a weapon such as a gun, knife, or explosive or as a result of an accident such as an automobile accident.

B. Fibrotic and Chronic Wounds

The disclosed microgels or PLPs can be used to treat chronic wounds. A chronic wound is a wound that does not heal normally. Wounds that do not heal within three months are often considered chronic. One embodiment provides administering an effective amount of the microgels or PLPs to a chronic wound to promote or enhance hemostasis.

The disclosed microgels and PLPs can also be used to treat fibrotic wounds. Fibrotic wounds have dysregulated healing and typically delayed healing. Fibrosis can be defined as the replacement of the normal structural elements of the tissue by distorted, non-functional and excessive accumulation of scar tissue. Another embodiment provides a method for treating fibrotic wounds by administering an effective amount of the disclosed microgels or PLPs to promote or enhance hemostasis.

C. Tumor Clotting

Solid tumors are known to undergo rapid angiogenesis to produce dysfunctional leaky vessels, which results in activation of the clotting cascade. One approach to limit nutrient delivery to the tumor is to inhibit blood supply by clotting the vessels by delivery of an effective dose of PLPs to induce clotting. In addition to this, PLPs can be used to deliver anti-tumor agents.

D. Drug Delivery

In some embodiments, the microgel compositions or PLPs can contain, be loaded with or functionalized with a bioactive agent. The microgels can be used to deliver an effective amount of one or more therapeutic, diagnostic, and/or prophylactic agents to an individual in need of such treatment. The amount of agent to be administered can be readily determine by the prescribing physician and is dependent on the age and weight of the patient and the disease or disorder to be treated.

The microgels are useful in drug delivery (as used herein "drug" includes therapeutic, nutritional, diagnostic and prophylactic agents), whether injected or surgically administered. The microgels are typically administered in an aqueous suspension (in water, saline, buffered saline, etc.).

The microgels can be used to as delivery vehicles for a number of active agent cargos including small molecules, nucleic acids, proteins, and other bioactive agents. The active agent or agents can be encapsulated within, dispersed within, and/or associated with the surface of the microgel. In some embodiments, the microgel packages two, three, four, or more different active agents for simultaneous delivery. In a preferred embodiment, the active agent is a cytokine or growth factor. Exemplary cytokines and growth factors include, but are not limited to members of the epidermal growth factor (EGF) family, transforming growth factor beta (TGF-beta) family, fibroblast growth factor (FGF) family, vascular endothelial growth factor (VEGF), granulocyte macrophage colony stimulating factor (GM-CSF), platelet-derived growth factor (PDGF), connective tissue growth factor (CTGF), interleukin (IL) family, and tumor necrosis factor-alpha family. Specific cytokines and growth factors include but are not limited to TGF-beta, EGF, TGF-alpha, VEGF, IGF-I, FGFs, IL-1beta, IL-4, IL-6, IL-8, IFN-alpha/beta, PDGF-BB, bFGF, and GM-CSF.

The active agent can be an anti-tumor agent or chemotherapeutic agent Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

The active agent-loaded microgels can be used to treat a variety of diseases and conditions, for example, cancer and chronic wounds. The compositions can be administered to the subject therapeutically or prophylactically.

III. Medical Devices

The disclosed fibrin-binding microgels or PLPs can be used to coat medical devices. Preferred medical devices that can be coated with the microgels include, but are not limited to medical devices that are used to inhibit or reduce bleeding or blood loss. Exemplary medical devices that can be coated with the micogels include clamps, staples and sutures.

A. Wound Dressing

The microgels can also be used with wound dressings. One embodiment provides a wound dressing having a layer of microgels on the wound dressing. The layer of microgels is configured to come into contact with the wound when the wound dressing is applied to a wound. The microgels can be impregnated in the wound dressing or coated on the wound dressing using conventional techniques. The wound dressing can be made of absorbent materials such as cotton of fleece. The wound dressing can also be made of synthetic fibers for example polyamide fibers. In certain embodiments, the wound dressing can have multiple layers including an adhesive layer, an absorbent layer, and moisture regulation layer. The wound dressing can also include antimicrobial agents, antifungal agents, and other active agents to promote wound healing such as cytokines and growth factors discussed above.

Another embodiment provides a method for treating a wound by administering an effective amount of the disclosed microgels to the wound to promote or induce hemostasis and then applying a wound dressing to the wound.

B. Sealants

The disclosed microgels or PLPs can be used as a sealant or tissue adhesive to seal ruptures or open wounds by promoting blood clotting. The microgels can be formulated as a dry powder or aqueous suspension and packaged into discrete packets or units to form a kit. Surgical hemostatic agents and sealants may be used as an aid to cease hemorrhage during surgery, either mechanically or by augmenting the body's response to coagulation. Their application can extend to the cessation of bleeding in areas where cautery is either contraindicated or difficult.

IV. Formulations and Administration

A. Pharmaceutical Compositions

Pharmaceutical compositions including the disclosed microgels or PLPs are provided. Pharmaceutical compositions can be for administration by parenteral (intramuscular, intraperitoneal, intravenous (IV) or subcutaneous) injection, or another suitable means. Compositions can be formulated in dosage forms appropriate for each route of administration.

In some embodiments, the compositions are administered systemically, for example, by intravenous or intraperitoneal administration, in an amount effective for delivery of the compositions to targeted cells, tissue, etc.

In certain embodiments, the compositions are administered locally, for example by injection directly into a site to be treated. In some embodiments, the compositions are injected or otherwise administered directly to diseased or disorder tissue, for example intratumor injection. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells and tissue include using infusion pumps (for example, from Alza Corporation, Palo Alto, Calif.) or incorporating the compositions into implants.

The microgels can be formulated in a physiologically acceptable carrier or vehicle, and injected or otherwise delivered into a tissue or fluid surrounding the target area.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired.

In a preferred embodiment the microgels are in a pharmaceutical composition including an aqueous solution suitable for parenteral delivery. The formulation can be in the form of a suspension or an emulsion. In general, pharmaceutical compositions are provided including effective amounts of cargo, and optionally include pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. Optional components of a pharmaceutical composition can be selected based on the composition of the microgel and its cargo. For example, if the cargo is cells, the additional agents in the pharmaceutical composition should be compatible with cell viability.

B. Dry Forms

The microgels or PLPs can be formulated in a dry or powdered form and applied topically to a site of injury or bleeding. Topical formulations of the microgels may include ointments, lotions, creams, gels, drops, suppositories, sprays, liquids and powders. Conventional pharmaceutical carriers, aqueous, powder or oily bases, or thickeners can be used as desired.

EXAMPLES

Example 1: Platelet-Like Particle Design and Characterization

Materials and Methods
Phage Biopanning Assays

Biopanning assays were performed with the domain antibody phagemid library that displays human derived single domain variable fragment antibody (sdFv/sdFv) containing only the heavy chain variable region (VH) of human IgG, Evans, et al., *World Journal of Surgery*, 34:158-163 (2010). The stock phage library was produced in a non-suppressor *E. coli* strain (TGI) and purified with polyethylene glycol according to the previously established protocol from Lee et al, McGwin, et al., *The Journal of Trauma*, 66:526-530 (2009). For biopanning assays, fibrin clots were formed in vitro by combining purified human fibrinogen, thrombin, and factor XIII at physiologically relevant concentrations (2 mg/mL); fibrin was allowed to polymerize for 1 hr prior to initiating biopanning assays. Clots were blocked with 5% powdered milk in phosphate buffer (137 mM NaCl, 2.7 mM KCl, 10 mM $Na_2HPO_4$, 2 mM $KH_2PO_4$; pH 7.4; MPBS). The purified phage library ($5 \times 10^{12}$ phage particles) was then incubated with fibrin clots allowing the phage to bind to the target. After removal of the supernatant, the fibrin clots were subjected to a series of rinses with PBS+0.1% Tween 20 (PBST) to rid the surface of non-specific binding phage. Next, a solution of soluble fibrinogen was overlaid on top of the fibrin clot to remove phage that recognize soluble fibrinogen and thereby increase the specificity of the fibrin-binding phage. The fibrin bound phage were then eluted from the fibrin clot, collected, and amplified. Subsequent rounds were repeated with an enriched population of eluted phage from the previous round. Outcome measurements after each round of screens included titers of initial phage stock, rinse solution, and eluted phage. After three rounds of binding selections, 96 clones for each library were selected and grown to produce phage and soluble antibody fragments according to the previously established protocol, McGwin, et al., *The Journal of Trauma*, 66:526-530 (2009). Identical screens were performed with the Tomlinson I and J libraries, which display human derived single chain variable fragment antibody (scFv) containing both the heavy chain variable region ($V_H$) and the light chain kappa variable region of human IgG, Evans, et al., *World Journal of Surgery*, 34:158-163 (2010).

Enzyme-Linked Immunosorbent Assay (ELISA)

Fibrin specificity was evaluated via enzyme-linked immunosorbent assay (ELISA). Soluble fragments possess a myc-tag, thus enabling binding detection via biotinylated anti-myc monoclonal in conjunction with streptavidin-HRP. Both fibrin and fibrinogen ELISAs were performed to identify clones with preferential binding affinity to fibrin over fibrinogen. Thin layers of fibrin were formed in the 96-well plates via layer-by-layer deposition of fibrinogen-thrombin-fibrinogen[3]. Separate fibrinogen-coated 96-well plates were prepared to run parallel ELISAs with the same scFv or sdFv clones. Each ELISA plate also contained positive controls (i.e., ubiquitin coated wells with clones specific to ubiquitin) and negative controls (i.e., random clones and non-antigen coated wells). Plates were blocked with 2% MPBS for 2 hrs a room temperature (RT). Freshly prepared scFv/sdFv supernatant was then incubated for 1 hr at RT. Plates were thoroughly rinsed with PBST prior to incubation with diluted anti-myc biotin (Sigma Aldrich; 1:2000) for 1 hr at RT. Plates were again thoroughly rinsed with PBST prior to incubation with Extravidin-HRP conjugate (Sigma Aldrich; 1:1000) for 1 hr at RT. HRP was developed using 1-Step Ultra-TMB-ELISA solution for ~15 min (Thermo Scientific); the reaction was stopped using 2N sulfuric acid and absorbance was quantified with a spectrophotometer (Molecular Devices; 450 nm).

Production of sdFvs

Select phage clones that demonstrated preferential binding affinity to fibrin were used to infect a non-suppressor *E. coli* strain (HB2151) to produce the soluble sdFv without the pIII fusion motif. HB2151 cells were grown at 37° C. and sdFv expression was induced with IPTG. Following induction, cells were grown at 28° C. for 20 h. The supernatant was collected, filtered and sdFv was then purified using protein A affinity chromatography (AKTA Purifier, GE Healthcare, Piscataway, N.J., USA).

SPR

Based on previous SPR protocols developed in the lab[4], a thin fibrin layer was immobilized on the surface of a gold SPR chip via layer-by-layer deposition of fibrinogen-thrombin-fibrinogen[3]. SdFvs were flowed across the fibrin surface and the binding interactions were evaluated and recorded. Additionally, antibody fragment binding interactions with a surface of immobilized fibrinogen was used to investigate the specificity to fibrin. All SPR data was examined and analyzed with Scrubber 2 and Clamp XP (Center for Biomolecular Interactions Analysis, University of Utah). Data simulation curves were generated based on a Langmuir 1:1 binding model assuming only a single ligand-analyte interaction.

SdFv-Microgel Synthesis and Characterization

Ultralow crosslinked (ULC) microgels (microgels) with highly deformable, dendritic architecture were prepared using standard precipitation polymerization techniques previously described, Clemetson, K. J., *Thrombosis Research*, 129:220-224 (2012). A 95% pNIPAm/5% AAc composition (poly(N-isopropylacrylamide-co-acrylic acid) was utilized for microgel synthesis which results in microscaffolds ~1-μm diameter in the swollen state. Co-polymerization with acrylic acid was utilized to allow for carboxylic acid chemoligation sites for sdFv attachment, Fries, et al., *British Journal of Anaesthesia*, 105:116-121 (2010); Granville-Chapman, et al., *Injury*, 42:447-459 (2011). Following synthesis, microgels were purified using ultracentrifugation and conjugated to fibrin specific sdFvs using standard EDC/NHS chemistry. For confocal fluorescence microscopy experiments, sdFvs were also labeled with maleimide-Alexa Fluor-488 following conjugation to the microgels. To determine basic microgels properties, the particles were characterized using dynamic light scattering to determine the hydrodynamic radius and atomic and force microscopy imaging to characterize morphology. Finally, to ensure that microgels coupled to fibrin-specific sdFvs retained fibrin-binding capabilities, binding of sdFv-micro gels to fibrin was determined through interferometry analysis utilizing the Fortebio Blitz system. Similarly as described for SPR analysis, for interferometry analysis, a thin fibrin layer was immobilized onto an amine reactive sensor chip (Ar2G, Fortébio).

Results

Upon initiation of clotting, platelets become activated, bind to nascent fibrin fibers, actively spread within the fibrin network and over time engage their actin-myosin machinery to contract the clot. Through the course of these events, platelets undergo significant shape changes. The disclosed platelet "bodies" made of ULC microgels are capable of undergoing large degrees of deformation. This is suggested by AFM images of microgels spread on the surface with a diameter of approximately 2 μm but an approximate height of only 4 nm. Increasing particle coverage on the surface resulted in particle deformation (away from a circular shape to maximize surface packing) and height distribution (presumably as a result of polymer chain coiling), further highlighting particle deformability. In order to impart a wound specific trigger to the microgels fibrin protofibrils were used as the molecular target for a directed evolution screen of randomized human sdFv.

Fibrin's amino acid sequence is distinguished from its soluble inactive precursor by less than 1% (i.e. loss of the first 16 residues from the two α-chains and 14 residues from the two β-chains of fibrinogen during thrombin activation). Thus, molecular discrimination of the two species is difficult. In order to meet this challenge, biopanning screens were performed with three different scFv and sdFv antibody phagemid libraries in vitro against fibrin clots derived from purified human fibrinogen, thrombin, and factor XIII at physiologically relevant concentrations. Fibrin-bound phages were challenged with soluble fibrinogen to remove cross-reactive species. Following standard procedures, prior to conducting each screen, the amplified and purified phage was titered. After each screen, the collected supernatants, washes, and elutions were titered to determine the distribution of phage bound and released at each step of the screen. Following the third round of screening, 96 clones for each library were selected, amplified, and their respective soluble antibody fragments produced and tested for binding to fibrin and fibrinogen.

Figure 3:
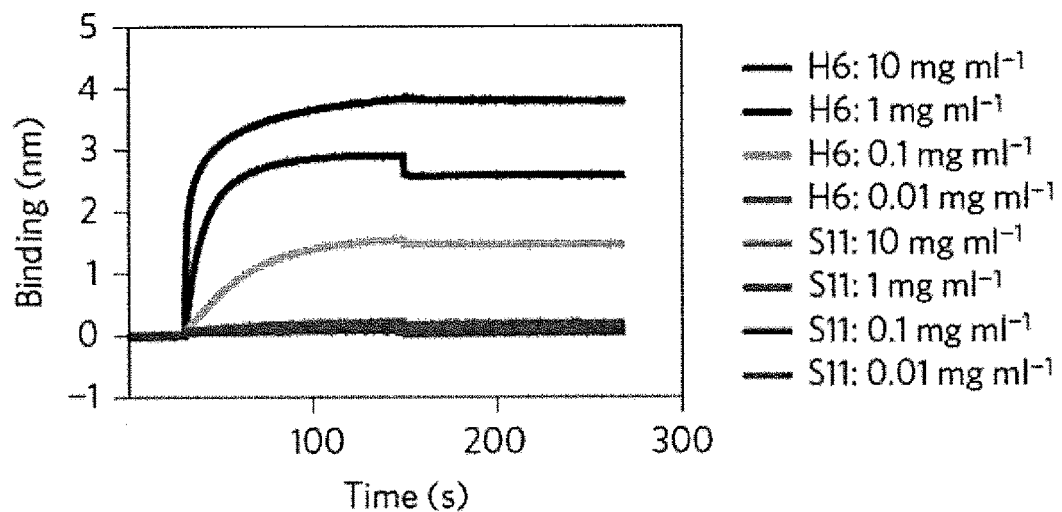
FIG. 3 is a graph of fibrin binding (nm) of H6 or S11 at the indicated concentrations versus time (s) on fibrin-coated surfaces.

The four most promising clones, based on their selectivity for fibrin over fibrinogen (clones A2, A6, B3 and H6) and a random clone (S11) were then evaluated through SPR analysis (FIGS. 2B-2K). Clone H6 was found to have the highest affinity for fibrin ($K_d$=199 nM), while, as expected, clone S11 was found to exhibit minimal fibrin binding. Clone H6 exhibited negligible binding to fibrinogen or BSA, highlighting the specificity of this sdFv. Clones H6 and S11 (negative control) were subsequently utilized for creation of PLPs. Interferometry analysis verified that sdFv-microgels maintained their fibrin-binding capabilities (FIG. 3). H6-microgels, the so-called PLPs, demonstrated increased binding to the fibrin layer with increasing concentrations, while no binding of S11-microgels (control PLPs) to fibrin was observed at any of the concentrations evaluated.

Example 2: PLPs Rescue Clotting Deficiencies of Platelet-Poor Plasma In Vitro

Materials and Methods
Dynamic In Vitro Clotting Assays
To characterize the effect of microgels on clotting in vitro, a endothelialized microfluidics device that accurately recapitulates the cellular, physical, and hemodynamic environment of microcirculation, was used as previously described, Jackson, et al., *Journal of Thrombosis and Haemostasis*: JTH 7 Suppl 1:17-20 (2009). For these experiments, clotting of platelet poor plasma (PPP) was analyzed in the absence or presence of fibrin-binding microgels of varying degrees of crosslinking in real time using confocal microscopy. As a control, clotting of platelet rich plasma (PRP) or PPP in the presence of non-fibrin binding microgels were also investigated. Microgels or buffer were added to PPP immediately prior to injection into the microfluidics device. To visualize clotting, PPP was spiked with Alexa Fluor-488 labeled fibrinogen. Endothelial cells were stained with Cell Mask Deep Red (Invitrogen) and microgels were labeled with Alexa Fluor 546. For experiments utilizing PRP, platelets were stained with Cell Mask Red (Invitrogen). Samples were flowed at 1.1 μL/min and imaged continuously for 20 min. Clotting overtime was characterized through imaging processing with Image J (NIH). Each microfluidic device is comprised of three regions of different flow rates, comprising four endothelialized channels.

Results

To first investigate the ability of our PLPs to recapitulate platelet function, clotting of platelet poor plasma was tested in relation to platelet-rich plasma in vitro. These dynamic clotting experiments were performed in an endothelialized microfluidic device that accurately recapitulates the cellular, physical, and hemodynamic environment of microcirculation, McGwin, G., Jr. et al. Reassessment of the tri-modal mortality distribution in the presence of a regional trauma system. *The Journal of trauma* 66, 526-530, doi:10.1097/TA.0b013e3181623321 (2009). As is widely accepted, it was found that normal human platelet-rich plasma under flow conditions displays robust formation of a fibrin-based clot in the presence of thrombin (factor IIa); whereas, the depletion of platelets (i.e., platelet-poor plasma) abrogates this native clotting response under flow. Supplementation of platelet-poor plasma with our PLPs successfully rescued fibrin clot formation in response to thrombin, even in 1:1 saline-diluted platelet-poor plasma triggered response was presumed to be an effect of multivalent presentation of the fibrin-specific sdFv only. Indeed, particle deformability does not appear critical to this effect since particles with higher degrees of crosslinking (decreased deformability) support thrombin-induced clot formation in platelet-poor plasma. Robust clotting was observed in the presence of H6-particle formulations of 2%, 4%, and 7% bisacrylamide (BIS) cross-linked microgels as well as polystyrene (PS) microparticles of the same dimensions.

Example 3: An Emergent Behavior: PLPs Induce Clot Contraction (590 Words)

Materials and Methods
Clot Polymerization/Degradation Assays
Thrombin-initiated fibrin polymerization and degradation assays were used to evaluate clotting rates and persistence in the presence of H6 and S11 (control) ULC microgels at different microgel and fibrinogen concentrations. Competing polymerization and degradation reactions were created with a 96 well plate, and a final volume of 100 μL per well. Two solutions were made, a fibrinogen-microgel solution that was loaded initially, and a thrombin-tPA (tissue Plasminogen Activator)-plasminogen solution that was added in a 1:1 volume ratio. Final concentrations in each well were 2 mg/mL microgel and 2 mg/mL of fibrinogen, 5 mMol Ca$^+$, 0.25 U/mL of human thrombin (Enzyme Research Laboratories, Inc., South Bend, Ind.), 0.29 µg/mL of tissue Plasminogen Activator (tPA), and 10.8 µg/mL of Plasminogen. The remainder of the volume in the thrombin/tPA/plasminogen solution was made up of 25 mM Hepes, 150 mM NaCl buffer. Turbidity curves were be generated from absorbance measurements (SpectraMax M2 Microplate Reader, Molecular Devices, Sunnyvale, Calif.) at 350 nm, with reads taken every thirty seconds.

Results

Figure 4A:
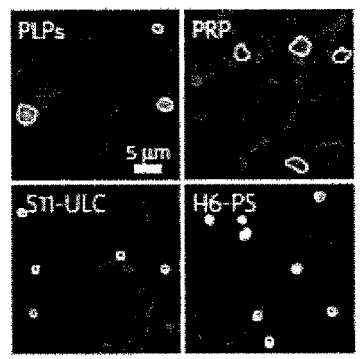
FIGS. 4A and 4B are maximum-intensity confocal images of fibrin clots formed from platelet-rich plasma (PRP) or platelet-poor plasma (PPP) in the absence or presence of PLPs or S11-ULCs. Fibrin, grey; microgels/platelets, circled.

To further characterize the nature of PLP-fibrin interactions, clot microstructure was analyzed via confocal microscopy by forming clots in the presence or absence of scFv-ULC microgels. Surprisingly, clots formed in the presence of PLPs were found to have a significantly altered clot structure. These clots were highly heterogeneous, containing regions of dense fibrin observed in conjugation with PLPs (FIG. 4A) with the dense features becoming more pronounced over time. These features were very similar to those observed from clots formed in platelet-rich plasma, although occurring on a different time scale. Clots formed in the presence of non-binding S11-ULC microgels were found to result in a more porous network compared to control (i.e. fibrin-only) clots, but the structure remained largely homogenous, and was similar to clots formed from fibrin-only.

These observations were suggestive of the PLPs ability to induce clot contraction, a significant function of platelets that has been shown to enhance clot stability, decrease fibrinolysis and is thought to contribute to subsequent wound healing, Jackson, S. P., Nesbitt, W. S. & Westein, E. Dynamics of platelet thrombus formation. *Journal of thrombosis and haemostasis JTH* 7 Suppl 1, 17-20, doi:10.1111/j.1538-7836.2009.03401.x (2009). Whereas many platelet-mimicking materials are capable of augmenting hemostasis, none of these current technologies are able to recapitulate the important platelet function of clot contraction.

The role of particle deformability was analyzed in the observed alterations in clot structure by comparing clots formed in the presence of PLPs, or 2% BIS, 4% BIS, 7% BIS microgels, or PS particles conjugated to the fibrin-specific sdFv and found that only PLPs significantly altered clot structure. Clots formed in the presence of 2 and 4%-BIS microgels displayed minor alterations in clot structure compared to control clots, while 7%-BIS microgels and PS particles appeared largely similar to control clots. These results suggest that fibrin binding coupled with high levels of particle deformability likely contribute to the significant alterations in clot structure observed.

Figure 4B:
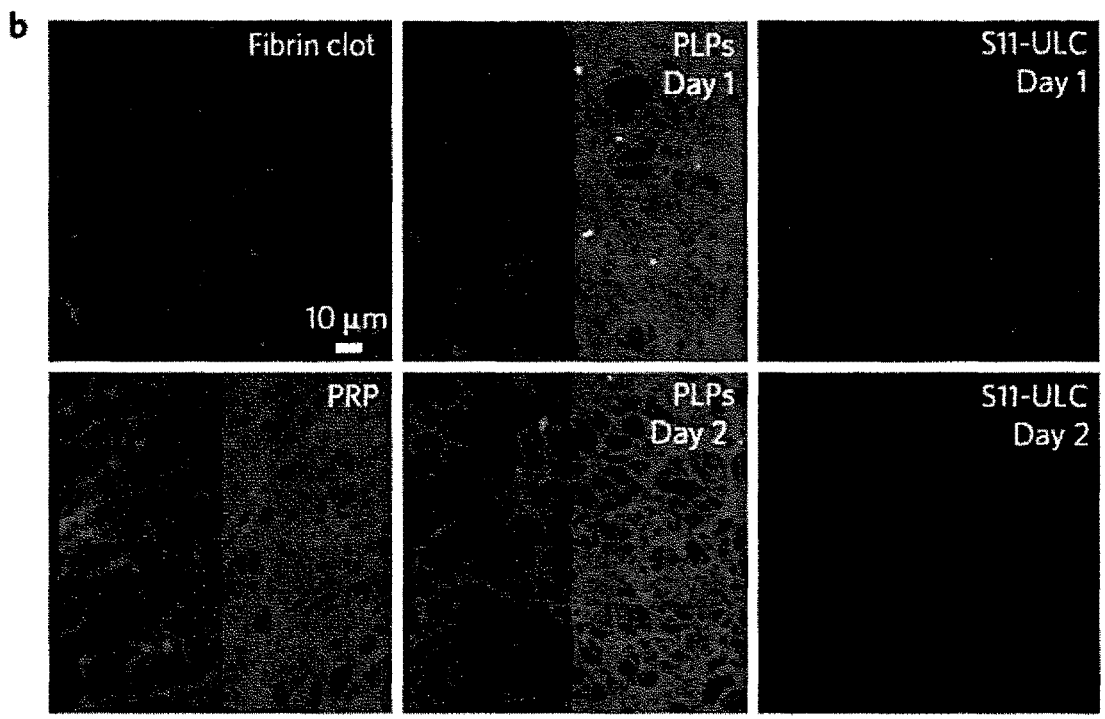
Figure 4C:
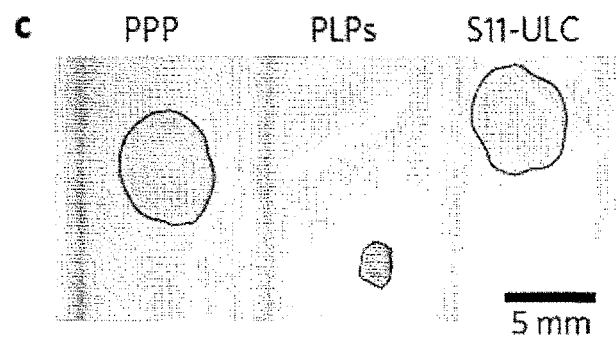
FIG. 4C shows the macroscopic collapse of clots from from PPP in the presence or absence of PLPs or S11-ULCs 48 h post polymerization.

Clot collapse was characterized at the macroscopic level by performing standard gross clot contraction experiments routinely utilized by platelet biologists, Thomas, et al., *BMC Cell Biology*, 8:46 (2007); Suzuki-Inoue, et al., *Thrombosis Research*, 120:251-258 (2007). It was expected that particle deformability would play a large role in the ability of fibrin-binding microgels to induce gross clot deformation and architectural changes. Clots were created through the addition of 1 U/mL thrombin (final concentration) to platelet-poor plasma containing microgels of varying crosslinking. Clot collapse was observed within 48 hours in the presence of PLPs but not under any other conditions tested (FIG. 4B). No significant differences in the overall degree of clot contraction were observed when comparing platelet-poor plasma containing PLPs and native platelet-rich plasma ((FIG. 4C). However, not surprisingly, the rate of PLP-induced collapse was significantly less than that observed in native platelet-containing clots. Because natural platelet mediated contraction decreases clot degradation rates, we analyzed clot degradation rates in the absence or presence of PLPs. Clots formed in the presence of PLPs were more resistant to degradation than control clots or clots formed in the presence of S11-ULC microgels (FIG. 4D), demonstrating that like natural platelets, PLPs significantly alter clot structure at both the microscopic and macroscopic levels resulting in physiologically relevant changes in the dynamics of clots. Because clot contraction was not observed in the presence of non-fibrin binding ULC microgels or in the presence of fibrin-binding BIS crosslinked microgels or hard PS particles, we conclude that, while enhancement of clotting in vitro only requires high affinity and multivalency for fibrin, particle deformability is critical to the ability of fibrin-binding particles to induce clot collapse. To fully recapitulate the hemostatic functions of platelets (enhancement of clotting and clot contraction following hemostasis) it appears that both high fibrin affinity and high particle deformability are required.

Example 4: PLPs Decrease Bleeding Times In Vivo and Home to Sites of Injury

Materials and Methods

Femoral Vessel Injury Model:

To test the efficacy of PLPs in hemostasis, a well-established rat femoral vessel traumatic injury model was used[13-15]. This model results in an easily visualized, continuous stream of blood flowing from the injury site. All protocols were approved by the Georgia Institute of Technology IACUC. Adult Sprague-Dawley male rats (200-250 g) were anesthetized with 5% isoflurane. Following anesthesia, an incision was made on the right hindlimb to expose the femoral vessels. A portion of the femoral vein was isolated from the surrounding connective tissue by placing a small piece of foil between the vessel and the underlying tissue. Following isolation of the vessel, the cavity will be irrigated with 0.9% irrigation fluid at 37° C. Animals were then administered 500 µl, of saline (vehicle), purified human factor VIIa (hFVIIa, 100 µg/kg the current standard of care, purchased from Innovative Research), PLPs (20 mg/mL) or S11-ULC microgels (20 mg/mL) via tail vein injection using a 24 gauge catheter. Six (6) animals were tested per condition. Following a 5 minute circulation time, injury was induced to the right femoral vein by piercing the vein with a 22 gauge needle. A gauze was lightly placed below the injury site to collect blood, allowing for better visualization of the injury site as well as measurement of total blood loss. Gauze were changed every ten seconds for the first 30 seconds following injury and then every 30 s until bleeding ceased. Bleeding time was defined as the time required for bleeding to cease for a minimum of 10 s. Following cessation of bleeding, animals were euthanized with carbon dioxide. Following cessation of bleeding, animals were euthanized and organs separated, fixed with 10% formalin, paraffin embedded and 5 µm sections were produced using a Microm 355H Microtome (Thermo Scientific). Co-localization of PLPs were characterized through immunofluorescence staining for the MYC-tag encoded on the sdFvs and through Martius Scarlet Blue (MSB) staining for fibrin in adjacent serial sections. For MYC-tag staining, samples were counter stained with Hoescht (Invitrogen) to visualize nuclei.

Statistical Analysis

All statistical analyses for bleeding time studies were performed with Prism software program (GraphPad, San Diego Calif.). Bleeding and blood weight data were statistically analyzed using repeated measures analysis of variance using the Tukey test at a 95% confidence interval.

Results

Figure 4D:
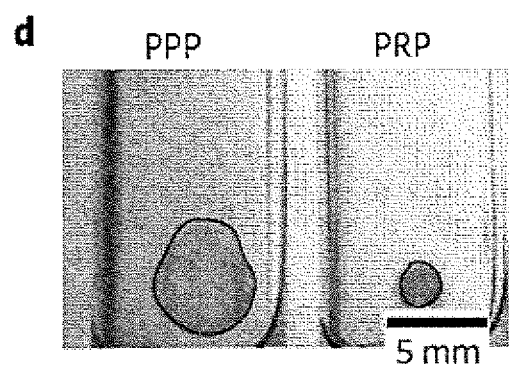
FIG. 4D shows the collapse of clots formed from PRP and PPP 4 h post-polymerization.
Figure 4E:
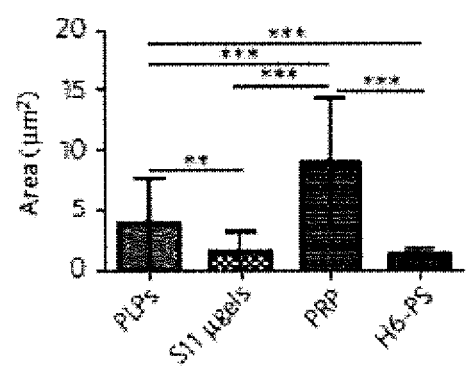
FIG. 4E is a graph showing the calculated spread area of PLPs, natural platelets, S11-ULCs and H6-PS particles within fibrin matrices. ($p<0.01$, $*p<0.001$).
Figure 5A:
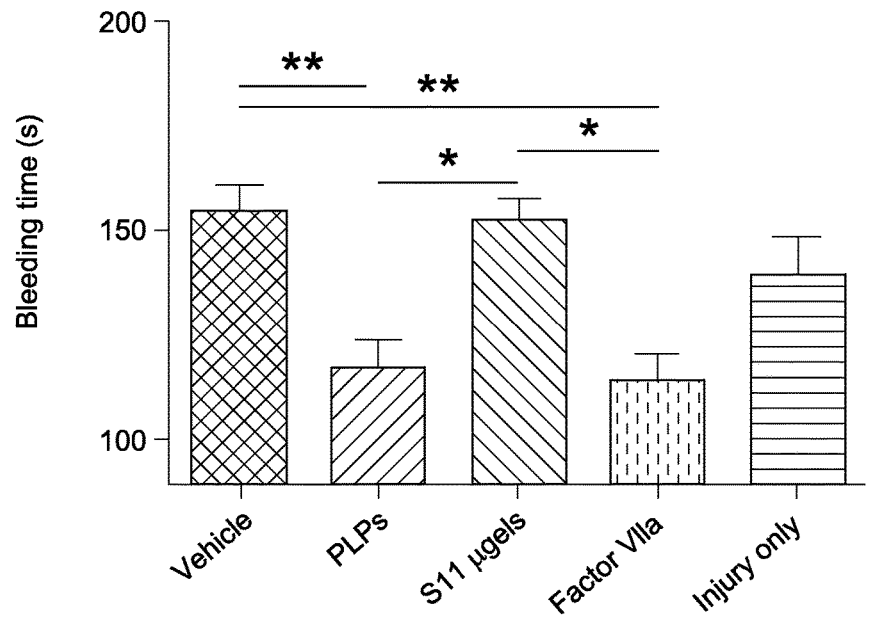
FIG. 5A is a bar graph of bleeding time (s) for rats administered saline (vehicle), PLPs, S11 microgels or Factor VIIa and following a 5 min circulation time.
Figure 5B:
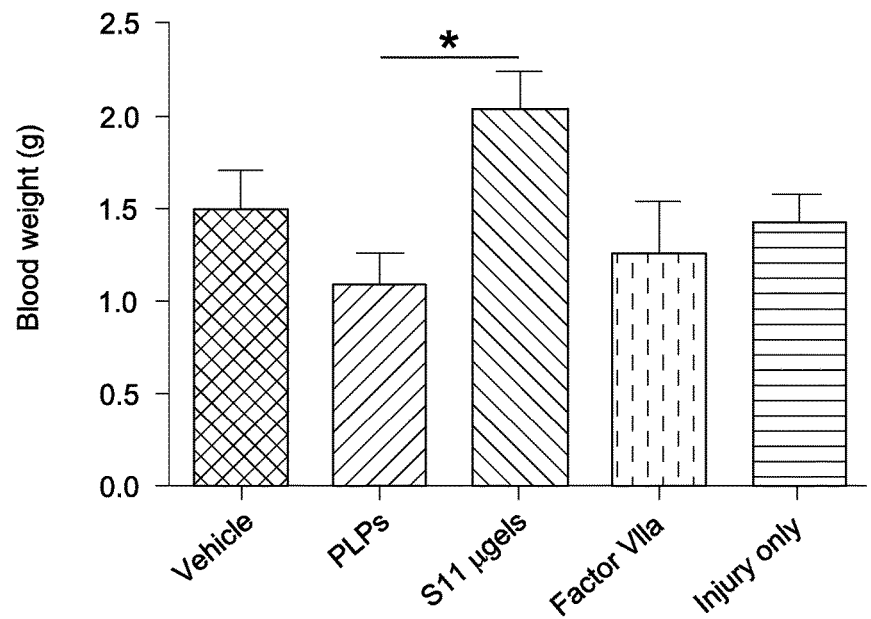
FIG. 5B is a bar graph of blood weight (g) for rats treated in 5A.
Figure 5C:
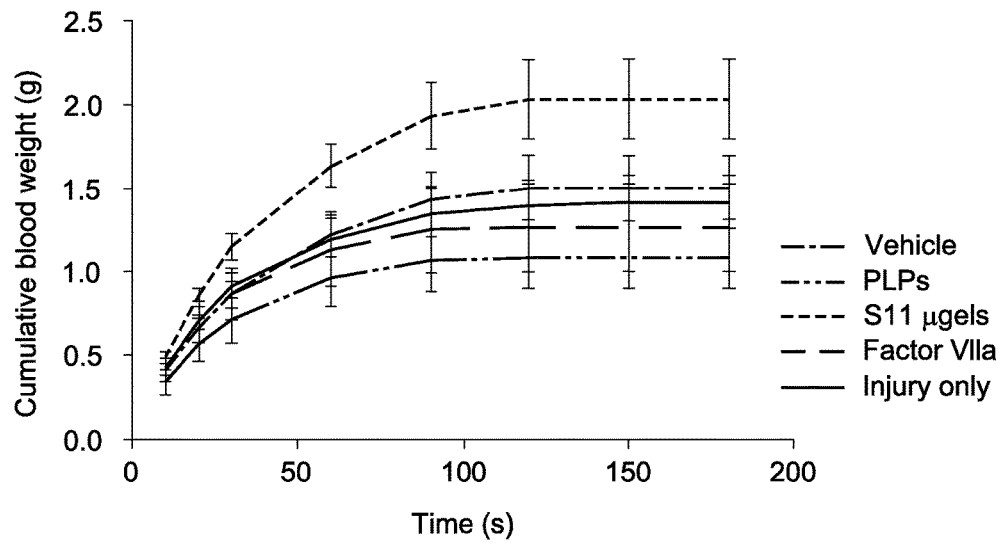
FIG. 5C is a line graph of cumulative blood weight (g) versus Time (s).

Based on in vitro studies, PLPs should recapitulate the important platelet functions of augmenting clotting in vivo and homing to sites of injury. To test the efficacy of PLPs in hemostasis, the rat femoral vessel traumatic injury model was used, Bertram, et al., *Science Translational Medicine*, 1 (11):11ra22, 16 pages (2009); Fuglsang, et al., *Blood Coagulation & Fibrinolysis: An International Journal in Haemostasis and Thrombosis*, 13:683-689 (2002); Ersoy, et al., *Advances in Therapy*, 24:485-492 (2007). Bleeding time following vessel injury was found to be significantly decreased in the presence of PLPs ($p<0.005$) compared to vehicle only. Bleeding time in the presence of PLPs were similar to those in the presence of the current clinical standard, Factor VIIa, and were 117+/−16 seconds and 114+/−17 seconds, respectively. S11-ULC microgels did not significantly affect bleeding times compared to vehicle only control (FIGS. 5A-5C) and total blood loss was significantly less in the presence PLPs compared to S11-ULC microgels ($p<0.05$). Analysis of bleeding dynamics also demonstrated that PLPs resulted in the slowest blood loss over time while S11-ULC microgels resulted in the most rapid blood loss over time (FIG. 4C-D). Wound tissue was analyzed post-mortem for fibrin and PLP deposition through MSB staining for fibrin and immunohistochemical staining for the MYC-tag encoded on the sdFvs. These analyses demonstrated colocalization of PLPs with fibrin clots, while minimal MYC staining was observed in S11-ULC microgels tissue samples. Furthermore, higher levels of fibrin staining were observed in vessels collected for animals receiving PLPs. These data indicate that PLPs are capable of localizing to the site of injury, enhance fibrin clot formation and decrease bleeding time and blood loss.

Example 5: PEG-Based Fibrin Binding Microgels

Materials and Methods

PEG-based microgels were polymerized in crosslinker free conditions as described above and then conjugated to the fibrin-binding scFv, H6. The size of the PEG unit of the monomer used was between 170 and 220 Da, Using this procedure PEG-based monomers in a size range from 100 to 700 nm can be prepared.

Results

Figure 6A:
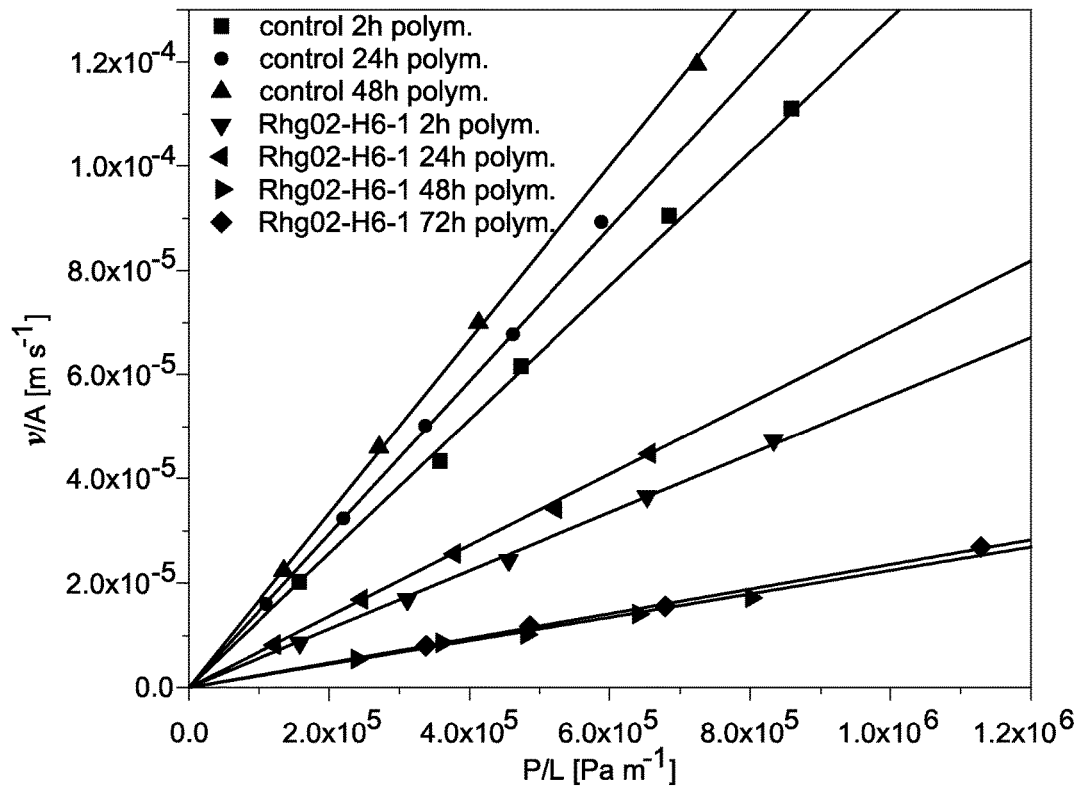
FIG. 6A is a line graph v/A [m-1 s-1] versus P/L [Pa m-1] showing permeability of clots formed in the absence or presence of PEG-H6 microgels.
Figure 6B:
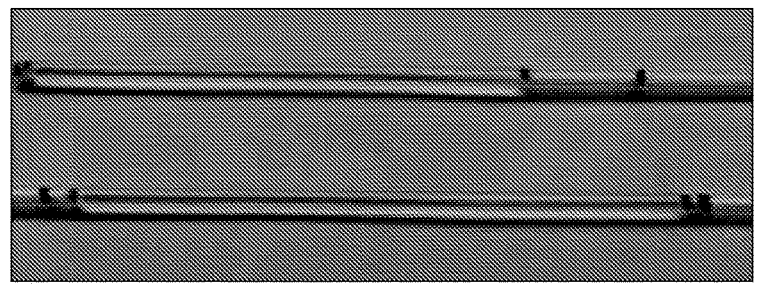
FIG. 6B is a photograph of showing clot contraction of fibrin clots in capillary tubes. Top: fibrin clot with H6-particles. Bottom: fibrin only. Black marks (with arrows) indicate the dimension of the fibrin clot at t=0 and blue marks (without arrows) indicated the clot dimensions at t=22 hours.
Figure 6C:
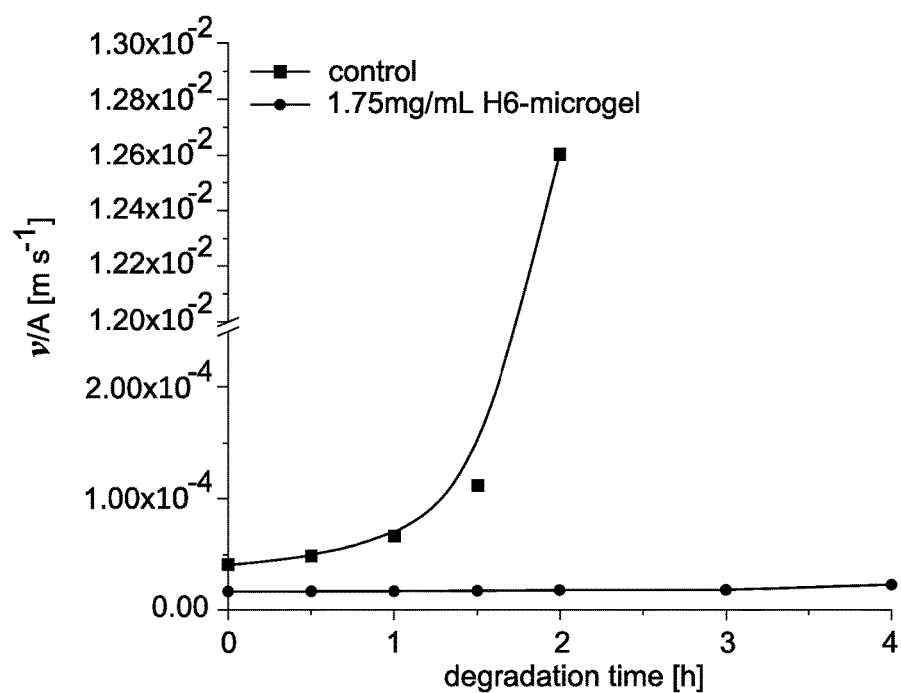
FIG. 6C is a line graph of v/A [m-1 s-1] versus degradation time [h] showing plasmin mediated degradation in the absence or presence of PEG-H6.

When introduced to a polymerizing fibrin network, like pNIPAM-based self-crosslinked microgels conjugated to H6, the PEG microgel-H6 constructs greatly alter fibrin structure at the microscopic level, induce gross clot contraction and decrease clot susceptibility to degradation. Analysis of clots formed in the presence of PEG-H6 microgels via confocal microscopy demonstrates that these clots have enhanced fibrin density compared to control clots and this density increases over the course of 24 hours post-polymerization. Permeation studies also show that the clots formed in the presence of PEG-H6 microgels are denser than the fibrin gel alone (FIG. 6A). Furthermore, gross clot contraction was observed 22 hours post-polymerization in clots formed in the presence of PEG-H6 microgels ((FIG. 6B). Finally, clot degradation studies demonstrate that clot degradation is decreased when clots are formed in the presence of PEG-H6, microgels (FIG. 6C). These results demonstrate that similar features of pNIPAM-based platelet-like particles, namely the highly innovative feature of clot contraction, can be recapitulated using PEG-based microgels formed under crosslinker-free synthesis conditions as a base material.

Example 6: H6 does not Bind to any Plasma Components Non-Specifically

Materials and Methods

H6 binding was determined through both qualitative and quantitative human plasma assays. The qualitative assay involved incubating either H6, the non-binding negative control, S11, or saline with human plasma at room temperature for 30 minutes. The plasma mixtures were subsequently incubated with protein A beads with the intent to pull down all IgG isotypes (including H6 and S11).

The quantitative assay involved coating a 96-well high-binding plate with five different 10-fold plasma dilutions. H6, S11, or a positive-control anti-fibrinogen antibody were incubated in these wells to allow for binding with plasma components to occur. All wells were set-up in triplicate. After washing away unbound nanobody or antibody and treating with appropriate secondary antibodies and ELISA reagents, the amount of H6, S11 or anti-fibrinogen antibody remaining in each well was measured spectrophotomerically in a plate reader. All readings were normalized to wells in which PBS was incubated with plasma.

Results

Figure 7A:
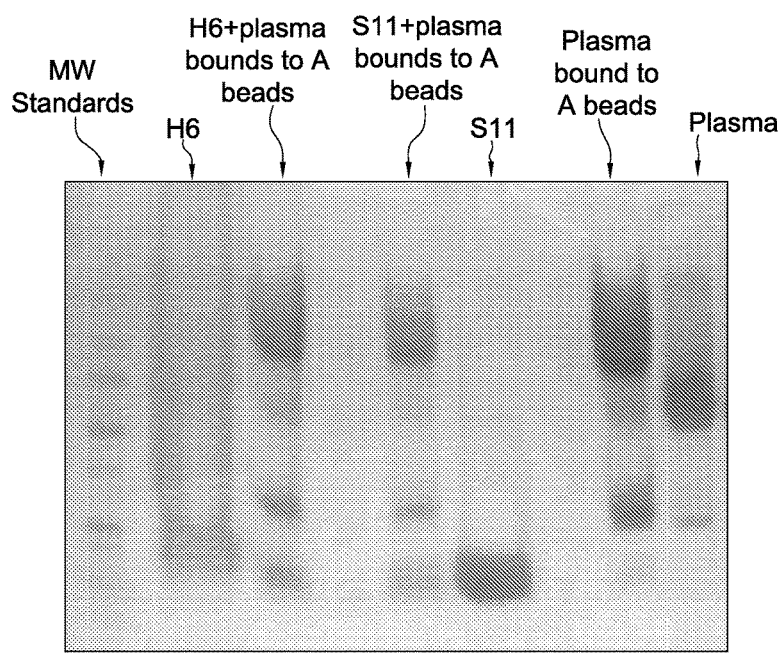
FIG. 7A is a photograph of a polyacrylamide gel showing that H6 does not bind to any plasma components non-specifically.

The eluants from the protein A pull down experiment were run on a polyacrylamide gradient gel to visualize any band shifts present in the H6-plasma solution that would indicate a binding interaction not present in the S11-plasma or saline-plasma solutions. No such band shifts were observed, indicating that H6 did not non-specifically bind to any human plasma components (FIG. 7A).

Figure 7B:
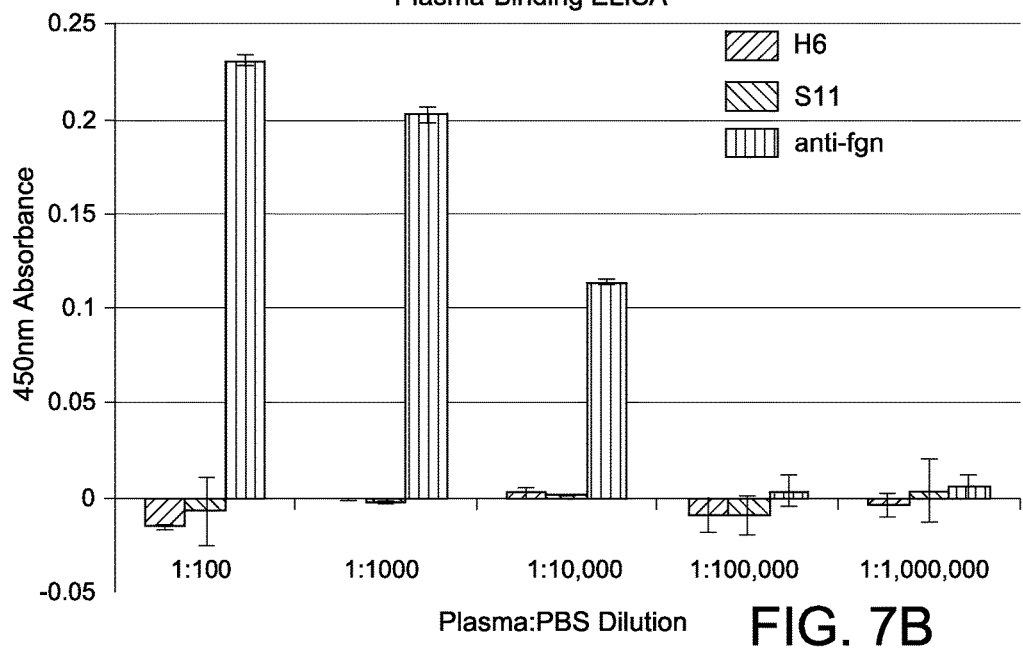
FIG. 7B is a bar graph of 450 nm Absorbance v Plasma:PBS dilutions 1:100; 1:1000; 1:10,000; 1:100,000; and 1:1,000,000 of from left to right for each dilution H6, S11 and anti-fgn.

ELISA results showed a dose-dependent binding response in the anti-fibrinogen antibody but negligible binding in both H6 and S11 (FIG. 7B). These results further imply that H6 does not bind to any component of human plasma non-specifically.

This was determined through ELISAs against plates coated with adsorbed fibrin D-Dimers or E Regions.

Figure 8A:
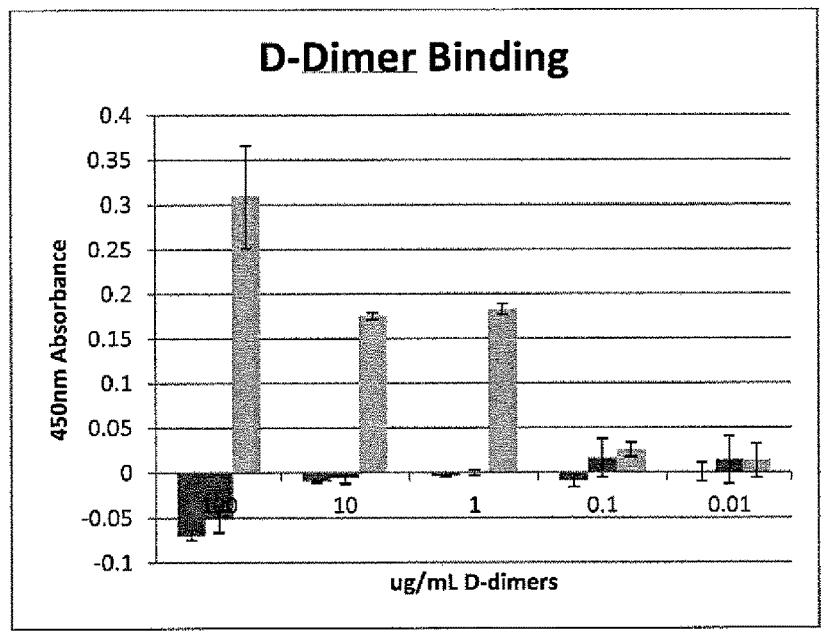
FIG. 8A is a bar graph of 450 nm Absorbance v µg/ml D-dimers for H6, S11 and anti-fgn.
Figure 8B:
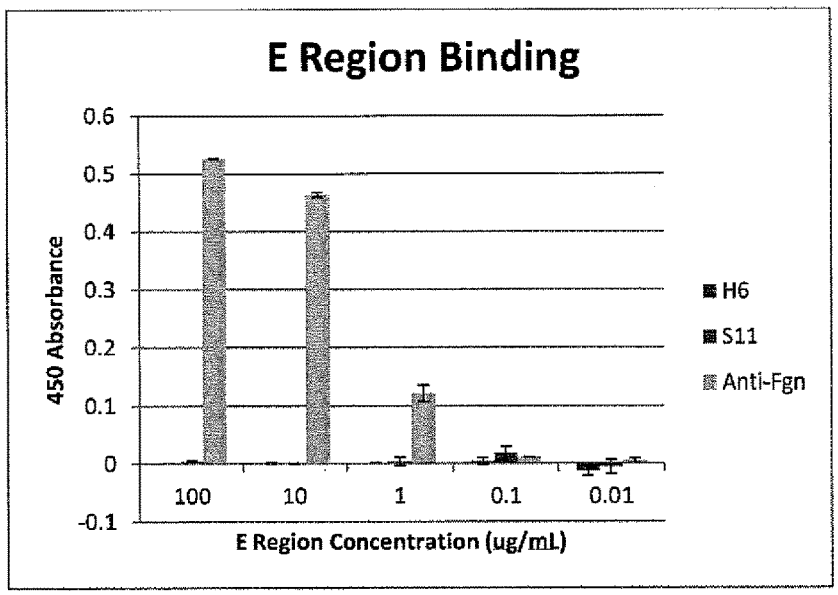
FIG. 8B is a bar graph of 450 nm Absorbance v ug/ml E region for H6, S11 and anti-fgn.

ELISA set-up and analysis was identical to that performed for the plasma-binding ELISA, the main exception being a substitution of human plasma dilutions for D-Dimer or E Region dilutions adsorbed to the 96-well plates. Both D-Dimer and E Region ELISA results (FIGS. 8A and 8B) showed dose-dependent binding of the anti-fibrinogen positive control but negligible binding of both S11 and H6. These results imply that H6 does not bind to any either of fibrin's degradation products.

Example 7: H6 does not Significantly Interfere with Fibrin Clot Polymerization

Materials and Methods

H6 interference with fibrin clot polymerization was determined through turbidity and clottability assays. The turbidity assay involved polymerizing physiological fibrin clots (2 mg/mL) in wells of a 96-well plate while taking absorbance measurements at 350 nm every 30 seconds. An increase in absorbance correlates to an increase in clot "cloudiness" which, in turn, indicates gelation. Turbidity of standard fibrin clots was compared to that of clots exposed to varying molar concentrations ranging from 1:1 to 1:1000 molar ratios of nanobody to fibrinogen.

The clottibility assay involved clotting purified fibrinogen or fibrinogen in the presence of H6 or S11, subsequently removing the gelled clot from solution, and measuring the amount of protein that was not incorporated into the clot. The same molar ratios of H6 and S11 to fibrinogen were investigated as per the turbidity assay. Soluble protein concentrations were measured using standard Quant-It assay protocols, and results were normalized to unpolymerized fibrinogen or fibrinogen-nanobody solutions of identical protein composition.

Results

Figure 9:
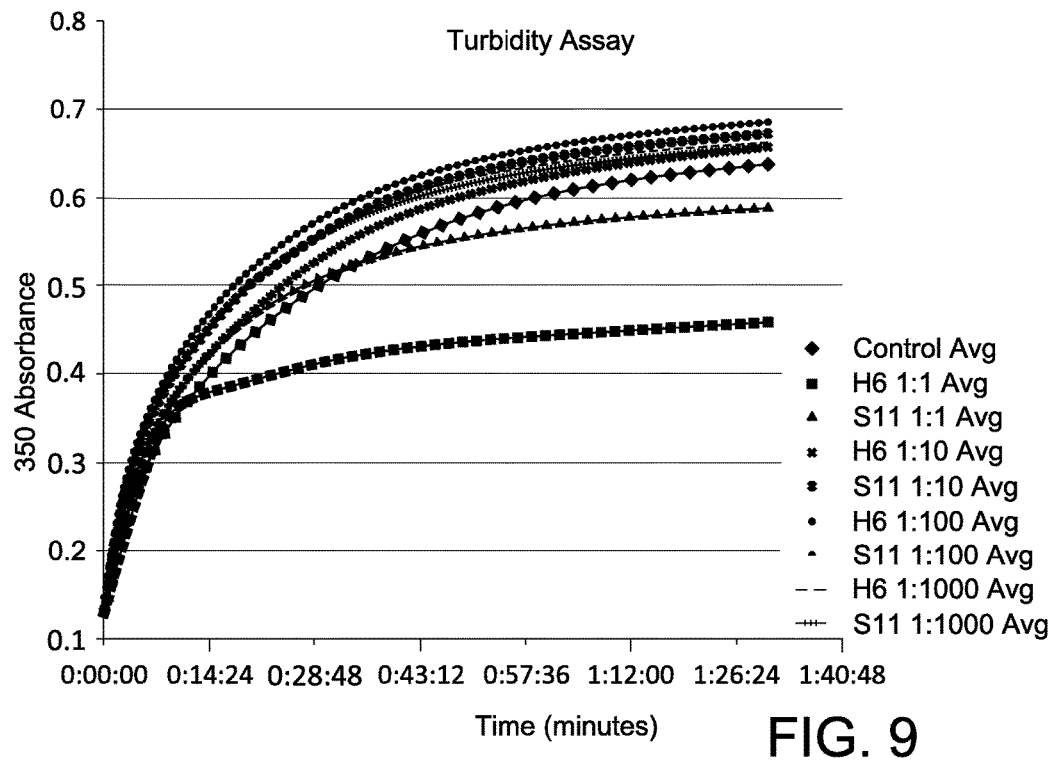
FIG. 9 is a line graph of 350 Absorbance versus time (minutes) showing the results of a Turbidity assay.

Turbidity results (FIG. 9) show that only at a very high molar ratio of H6 to fibrinogen (1:1), which would be difficult to achieve physiologically, was there any notable difference in turbidity readings, although high variability prevented these differences from being significant. All other molar ratios of H6 or S11 mixed with fibrinogen produced turbidity readings indistinguishable from physiological fibrin controls.

Figure 10:
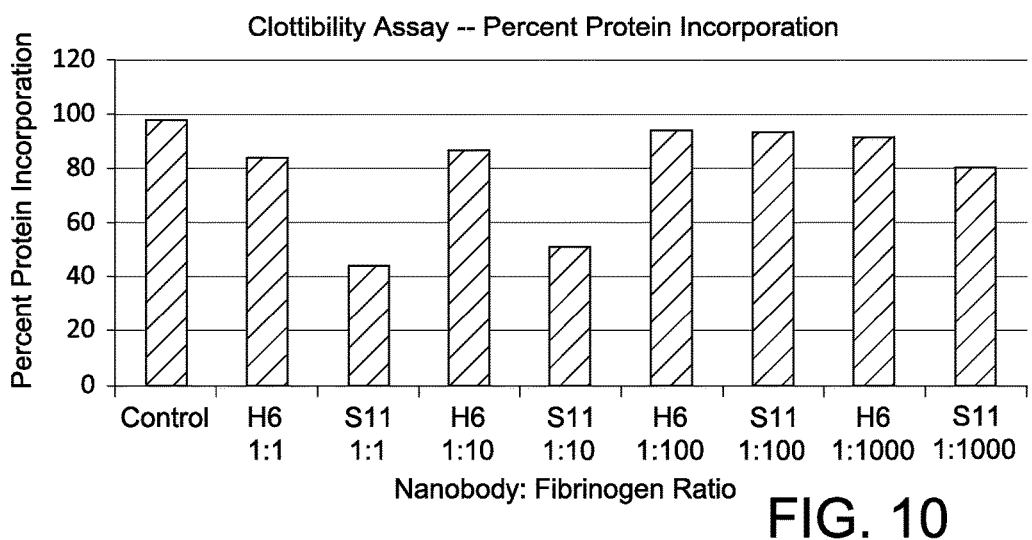
FIG. 10 is a bar graph of percent protein incorporation versus nanobody:fibrinogen ratio showing the ability of H6 to bind to fibrinogen in various states of unfolding.

Clottibilty results (FIG. 10) indicate greater than 80% protein incorporation for all H6 concentrations tested. Control fibrin clots possessed a clottibility of 97%. Notably, Quant-It cannot distinguish fibrinogen from H6 or S11. Therefore, lower protein incorporation seen among higher H6/S11 groups is likely indicative of large amounts of S11 or H6 that were never incorporated into the clots. The less than 50% protein incorporation seen in 1:1 and 1:10 S11 negative controls highlights this likelihood. Therefore, it is reasonable to assume that the percent of fibrinogen incorporation measured for any group containing H6 or S11 is was artificially lowered by an excess of unbound H6 or S11. A fibrinogen incorporation of 80% or higher for all H6 concentrations tested indicates that H6 does not significantly interfere with clot polymerization.

Example 8: H6 Binding to Fibrin is Conformation-Dependent

Materials and Methods

Characterization of H6 binding to fibrin was determined through a series of experiments designed to test the ability of H6 to bind fibrinogen in various states of unfolding.

In the first experiment ELISAs, as described previously, were performed comparing the ability of H6 to bind fibrinogen that was either passively adsorbed to a glass surface or immobilized to a glass surface, the assumption being that fibrinogen exists in a more unfolded state when adsorbed in comparison to when its immobilized on a surface.

Results

Though H6 binding to both surfaces was weak, there existed a notable dose-dependent decrease in binding of H6 to immobilized fibrinogen in comparision to adsorbed fibrinogen.

This experiment was repeated comparing the ability of H6 to bind fibrinogen passively adsorbed to a plastic surface after having been heat-denatured, or not, with the assumption being that heat-denatured fibrinogen exists in a more unfolded state than that of fibrinogen that was not heat-denatured. Results of this experiment showed weak binding of H6, but a notable dose-dependent enhanced ability of H6 to bind heat-denatured fibrinogen over un-denatured fibrinogen.

Finally, this experiment was repeated to compare the ability of H6 to bind fibrinogen that was passively adsorbed after no treatment, heat denaturing, heat denaturing plus reduction of sulfide bonds, or just reduction of sulfide bonds. The assumption is that reduction of sulfide bonds within a fibrinogen molecule in addition to heat denaturing result in an even greater extent of molecular unfolding than compared to heat denaturing alone. The results of this experiment indicate that H6 the ability to bind fibrinogen in a dose-dependent manner is positively correlated to the degree of unfolding in the fibrinogen molecule.

Taken together, the results from these three experiments investigating the ability of H6 to bind unfolded fibrinogen indicate that the binding sequence for which H6 possesses an affinity exists within the native fibrinogen molecule and that its ability to recognize this motif is a conformation-dependent phenomenon.

Table 1 below, as replicated from the Review article titled, "The Evolution of Fibrin-Specific Targeting Strategies" shows the unique status of H6. The table lists every distinct form of fibrin-specific targeting technology that has been discovered, to date. Technologies including EP-2104R, Tn6-21, FibPep, EPep, MH-1, NIH lh1 0, NIB 5F3 DI3B6/22-80B3, and ThromboView possess a binding affinity for one of fibrin's degradation products, which significantly reduces targeting specificity since these products are likely to circulate in the bloodstream due to a variety of confounding pathologies.

Technologies including SP2, GPRPFPAC, Anti-Fgn 17, T2G1, 59D6, and Centocor C22A possess an affinity for either a fibrin polymerization hole or knob region. They are therefore likely to inhibit fibrin's ability to clot, experience a reduction of fibrin-binding ability in the presence of anticoagulants, and/or target only clots that have formed recently. Technologies highlighted in blue bind to locations in fibrin that are also the binding sites of other physiological molecules. These technologies are therefore likely to interfere with or compete with other physiological fibrin-binding entities. Finally, technologies including CLT-1 and CREKA are known to bind to more complex fibrin structures associated with other molecules.

The Yan scFv has never been fully characterized, so it is not known where on fibrin it actually binds. Nevertheless, it is known to be larger than H6, and it only binds to fibrin very weakly.

The monoclonal antibody termed 102-10 mAb is the only other existing technology known to bind specifically to fibrin in a conformation-dependent manner. The exact affinity of 102-10 mAb has not been reported. Nevertheless, it currently only exists as a full-length antibody which implies that it possesses immunogenicity concerns and that it is excessively large for many fibrin-targeting applications.

H6 therefore constitutes an entirely unique fibrin-binding entity. It is one of two molecules that are known to bind polymerized fibrin in a conformation-dependent manner, and the only antibody domain fragment that can do so. Notably, H6 does not bind to any of fibrin's degradation products or polymerization sites.

TABLE 1

| Binding Molecule | Affinity | Molecular Weight (Da) | Molecule Type | Ligand | References |
|---|---|---|---|---|---|
| Evolutionary Approach | | | | | |
| H6 | 199 nM | 17,492 | sdFv | Cross-linked Fibrin Clot | 78 |
| SP2 | 44 nM | 45,570 (scFv) | scFv, mAb, or F(ab')$_2$ | Knob 'A' | 26 |
| EP-2104R, Tn6-21, FibPep, EPep, | 1.6 uM | 1385 | peptide | D-Dimer/Fibrin | 1, 71-76 |

TABLE 1-continued

| Binding Molecule | Affinity | Molecular Weight (Da) | Molecule Type | Ligand | References |
|---|---|---|---|---|---|
| CLT-1 | Not Reported | 1120 | peptide | Fibrin-fibronectin complexes | 67-70 |
| CREKA | Not Reported | 606 | peptide | Fibrin-fibronectin complexes | 6, 62-66 |
| Yan ScFv | ~6:1 fibrin preference | 27,000 | scFv | Fibrin Clot | 77 |
| Biological Mimicry Approach | | | | | |
| GPRPFPAC | 25 uM | 844 | peptide | Holes 'a' and 'b' | |
| Fibronection N-terminal FBD | 18 nM | 25,000 | peptide | Fibronectin-binding domain | 55, 56 |
| Kringle-1 | 12-17 uM | 10,000 | peptide | Plasminogen binding-domain | 7, 48-50 |
| α2-AP | Covalent Bond | 1600 | peptide | Anti-plasminogen binding domain | 51, 52 |
| Shotgun Approach | | | | | |
| MH-1 | 0.67 nM | ~150,000 | mAb | Freeze fractured fibrin, D-Dimer | 36 |
| NIH 1H10 | 3.9 nM | 96,000 | mAb | Freeze-fractured fibrin, E Region | 35 |
| NIB 5F3 | 4.3 nM | ~150,000 | mAb | E-Fragment | 35 |
| 102-10 mAb | Not Reported | ~150,000 | mAb | Bβ (149-234) | 37 |
| A Priori Approach | | | | | |
| DI3B6/22-80B3, ThromboView | 1.6 nM | ~55,000-110,000 | F(ab')₂ or Fab' | D-Dimer | 32, 33 |
| Anti-Fgn 17 | Not Reported | ~150,000 | mAb | Knob 'A' (GPRVVE) | |
| T2G1 | Not Reported | 50,000-150,000 | mAb or Fab' | Knob 'B' | 14, 17 |
| 59D8 Centocor C22A | Not Reported | 36,000-150,000 | mAb, Fab or scFv | Knob 'B' | 5, 9, 15, 18 |

What is claimed is:

1. An ultra-low crosslinked microgel comprising an ultra-low crosslinked polymer having <0.5% crosslinking densities, wherein the microgel comprises a binding moiety specific for fibrin conjugated to the exterior of the microgel, and wherein the binding moiety comprises the amino acid sequence of SEQ ID NO:1 (H6) and has little or no binding to soluble fibrinogen under physiological conditions compared to its binding to fibrin.

2. The microgel of claim 1, wherein the polymer is poly(N-isopropylacrylamide-co-acrylic acid).

3. The microgel of claim 2, wherein the composition of the polymer is 95:5 molar ratio of N-isopropylacrylamide to acrylic acid.

4. The microgel of claim 1, wherein the binding moiety specific for fibrin is present on the surface of the microgel at a density of $9.98 \times 10^{-11}$ mg/particle.

5. The microgel of claim 1, wherein the microgel is formed under crosslinker-free synthesis conditions.

6. The microgel of claim 1, wherein the microgel has a diameter of about 1 μm in solution.

7. A pharmaceutical composition comprising:
a microgel according to claim 1; and
a pharmaceutically acceptable excipient.

8. A kit comprising:
any one of the microgels according to claim 1 formulated into a unit dose; and
a bandage.

9. A wound dressing comprising:
a dressing comprising any one of the microgels according to claims 1-2, 3, and 4-6.

10. A medical device coated with the microgel of claim 1.

11. The medical device of claim 10, wherein the medical device is selected from the group consisting of a clamp, suture, and staple.

* * * * *

UNITED STATES PATENT AND TRADEMARK OFFICE
CERTIFICATE OF CORRECTION

PATENT NO. : 10,195,304 B2  
APPLICATION NO. : 15/035831  
DATED : February 5, 2019  
INVENTOR(S) : Thomas H. Barker et al.

Page 1 of 1

It is certified that error appears in the above-identified patent and that said Letters Patent is hereby corrected as shown below:

In the Specification

At Column 1, Lines 16 to 19, please change "Government support under Contract Number EB013743 awarded by the National Institutes of Health, Contract No. W81XWGH110306 awarded by the U.S. Army. The Government" to -- government support under grant number EB013743 awarded by the National Institutes of Health and W81XWH-11-1-0306 awarded by the United States Army Medical Research and Materiel Command. The government --

Signed and Sealed this  
Twenty-first Day of May, 2019

Andrei Iancu  
*Director of the United States Patent and Trademark Office*